United States Patent
Chen et al.

(10) Patent No.: US 11,246,742 B2
(45) Date of Patent: Feb. 15, 2022

(54) ORAL DEVICE TO ELIMINATE AIR SPACE IN ORAL CAVITY

(71) Applicant: Somnics, Inc. (Taiwan), Hsinchu (TW)

(72) Inventors: Chung-Chu Chen, Hsinchu (TW);
Yin-Ruei Chen, Hsinchu (TW);
Ming-jian You, Hsinchu (TW);
Wen-Yen Huang, Hsinchu (TW)

( * ) Notice: Subject to any disclaimer, the term of this patent is extended or adjusted under 35 U.S.C. 154(b) by 306 days.

(21) Appl. No.: 14/760,429

(22) PCT Filed: Jan. 10, 2014

(86) PCT No.: PCT/US2014/011129
§ 371 (c)(1),
(2) Date: Jul. 10, 2015

(87) PCT Pub. No.: WO2014/110432
PCT Pub. Date: Jul. 17, 2014

(65) Prior Publication Data
US 2015/0342778 A1 Dec. 3, 2015

Related U.S. Application Data

(60) Provisional application No. 61/751,559, filed on Jan. 11, 2013.

(51) Int. Cl.
*A61F 5/56* (2006.01)
(52) U.S. Cl.
CPC .................................... *A61F 5/566* (2013.01)
(58) Field of Classification Search
CPC ... A61C 17/02; A61C 17/0208; A61C 17/043; A61C 5/14; A61C 7/04; A61C 5/82;
(Continued)

(56) References Cited

U.S. PATENT DOCUMENTS 2,068,496 A * 1/1937 Linghammar ............ A47L 9/02
15/415.1
2,599,521 A 6/1952 Berman
(Continued)

FOREIGN PATENT DOCUMENTS

CN 101143115 A 3/2008
EP 1 192 928 A2 4/2002
(Continued)

OTHER PUBLICATIONS

Chinese Office action for Application No. 201480001034.0 with English translation, dated Sep. 2, 2015, 16 pages.
(Continued)

*Primary Examiner* — Camtu T Nguyen
(74) *Attorney, Agent, or Firm* — Stinson LLP

(57) ABSTRACT

This invention provides devices and systems and methods therefrom for properly controlling negative pressure applied to oral cavity, facilitating breathing and treating sleep apnea and snoring. The systems comprise a negative pressure system providing a vacuum source and an oral device comprising a shield, a tube passing through the shield, a flexible negative pressure deliverable part connected to the shield or the tube, an optional tongue protector, where the negative pressure deliverable part is conformable to the contour of the upper palate. Negative pressure is delivered to the front and back zones inside the oral cavity via the negative pressure deliverable part to eliminate air space in the oral cavity.

28 Claims, 20 Drawing Sheets

(58) Field of Classification Search
CPC ........... A61C 5/90; A61C 17/04; A61C 17/14; A61F 5/56; A61F 5/566; A61F 2005/063; A61M 16/0497; A61M 16/0493; A61M 16/049; A61M 16/049; A61M 16/0488

USPC .............................................. 433/91–97, 140

See application file for complete search history.

(56) References Cited

U.S. PATENT DOCUMENTS

| | | | | |
|---|---|---|---|---|
| 2,937,445 | A | * | 5/1960 | Erickson ............... A61C 17/08 433/93 |
| 2,939,445 | A | * | 6/1960 | Sterner ................... F02M 1/10 261/39.3 |
| 3,091,859 | A | * | 6/1963 | Baughan ............... A61C 17/08 433/94 |
| 4,063,552 | A | * | 12/1977 | Going ................. A63B 71/085 128/861 |
| 4,368,737 | A | * | 1/1983 | Ash ....................... A61M 1/285 604/175 |
| 5,071,347 | A | * | 12/1991 | McGuire ............... A61C 17/08 433/91 |
| 5,094,616 | A | * | 3/1992 | Levenson ............. A61C 17/08 433/93 |
| 5,361,921 | A | | 11/1994 | Burns |
| 5,465,734 | A | | 11/1995 | Alvarez et al. |
| 5,533,523 | A | * | 7/1996 | Bass, Jr. ........... A61M 16/0488 128/859 |
| 5,692,523 | A | * | 12/1997 | Croll ................... A63B 71/085 128/859 |
| 5,876,199 | A | * | 3/1999 | Bergersen ............... A61C 7/08 433/6 |
| 5,957,133 | A | | 9/1999 | Hart |
| 6,186,783 | B1 | | 2/2001 | Brassil et al. |
| 7,451,766 | B2 | | 11/2008 | Alvarez et al. |
| 2001/0044593 | A1 | * | 11/2001 | Lundy ................... A61M 1/062 604/74 |
| 2003/0208149 | A1 | | 11/2003 | Coffey |
| 2005/0166928 | A1 | | 8/2005 | Jiang |
| 2005/0217678 | A1 | * | 10/2005 | McCormick ...... A61M 16/0841 128/206.29 |
| 2006/0096600 | A1 | | 5/2006 | Witt et al. |
| 2007/0277818 | A1 | | 12/2007 | Chen |
| 2008/0216839 | A1 | * | 9/2008 | Rutter ............... A61M 16/0418 128/207.14 |
| 2009/0120446 | A1 | | 5/2009 | Vaska et al. |
| 2010/0044593 | A1 | * | 2/2010 | Jansen ................ G03F 7/70341 250/492.2 |
| 2010/0268107 | A1 | | 10/2010 | de Heer |
| 2010/0304324 | A1 | * | 12/2010 | Dragan .................... A61C 5/90 433/31 |
| 2011/0073119 | A1 | * | 3/2011 | Chen ....................... A61F 5/566 128/848 |
| 2011/0220124 | A1 | * | 9/2011 | Vaska ..................... A61F 5/566 128/848 |
| 2011/0259346 | A1 | | 10/2011 | Tsuiki et al. |
| 2012/0132215 | A1 | | 5/2012 | Vaska et al. |
| 2013/0213409 | A1 | | 8/2013 | Podmore et al. |
| 2014/0034064 | A1 | * | 2/2014 | Chen ................. A61M 16/0493 128/848 |

FOREIGN PATENT DOCUMENTS

| | | |
|---|---|---|
| EP | 1 913 968 A1 | 4/2008 |
| JP | 2008-183388 A | 8/2008 |
| TW | 318428 U | 9/2007 |

OTHER PUBLICATIONS

Chinese Notification of the Grant of the Patent Right for Application No. 201480001034.0 with English translation, dated May 24, 2016, 4 pages.

Taiwanese Office action for Application No. 103 101 121 with English translation, dated Dec. 7, 2015, 18 pages.

Taiwanese Notice of Allowance for Application No. 103 101 121 with English translation, May 24, 2016, 3 pages.

International Search Report for PCT Application No. PCT/US2014/011129, dated Jul. 17, 2014, 2 pages.

Final Office action from U.S. Appl. No. 14/153,336, dated Jun. 3, 2016, 19 pages.

Australian Patent Examination Report No. 1 for Application No. 2014205191, dated Mar. 16, 2016, 3 pages.

Non-Final Office action for U.S. Appl. No. 14/153,336, dated Apr. 11, 2017, 21 pages.

Non-Final Office action from U.S. Appl. No. 14/153,336, dated Feb. 8, 2018, 23 pages.

Non-Final Office action for U.S. Appl. No. 14/153,336, dated Aug. 12, 2015, 18 pages.

Final Office action for U.S. Appl. No. 14/153,336, dated Nov. 24, 2020, 25 pages.

Office Action dated Jun. 26, 2020 U.S. Appl. No. 14/153,336, 25 pages.

\* cited by examiner

FIGS. 2A-B
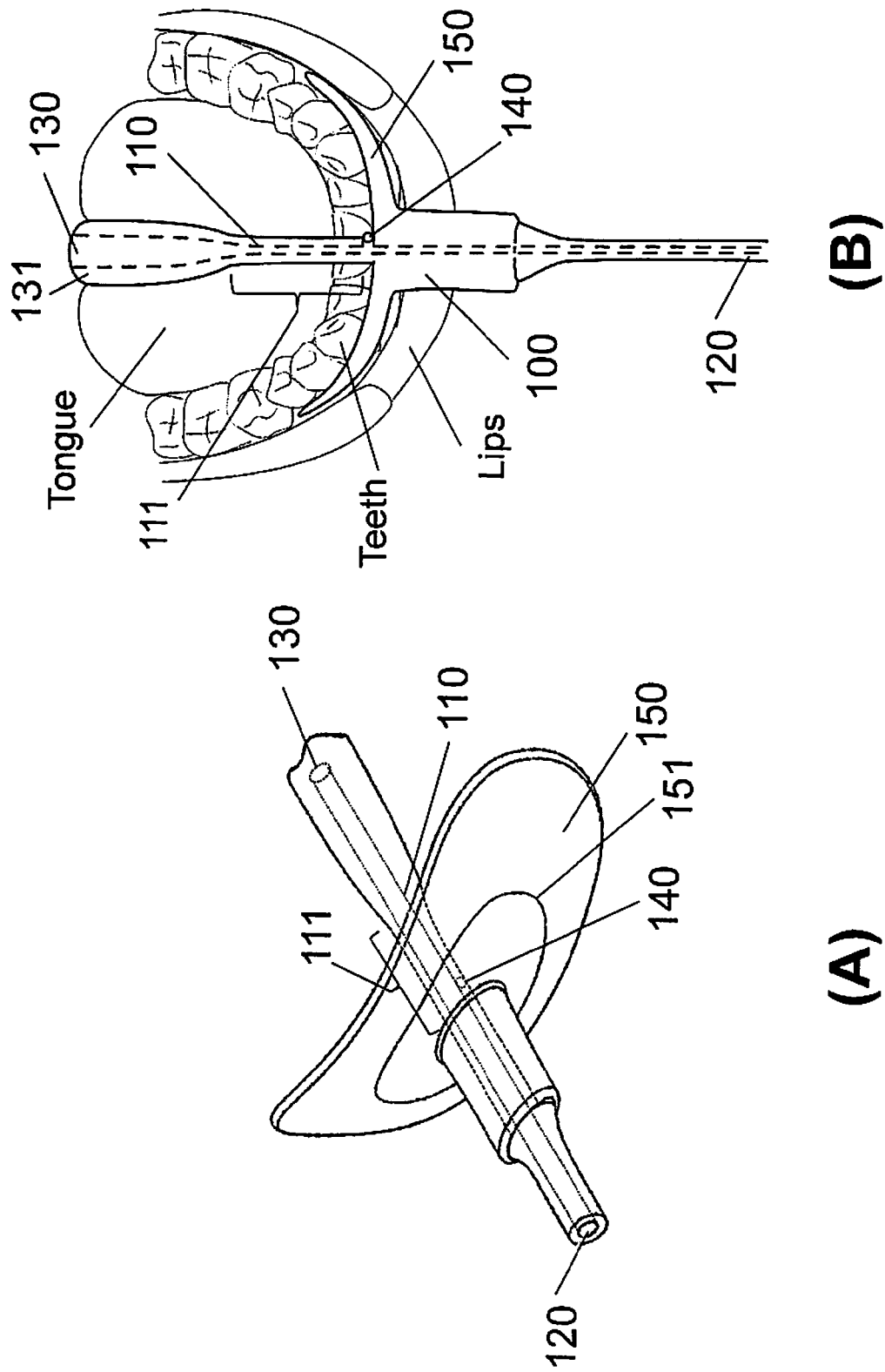

FIGS. 3A-D
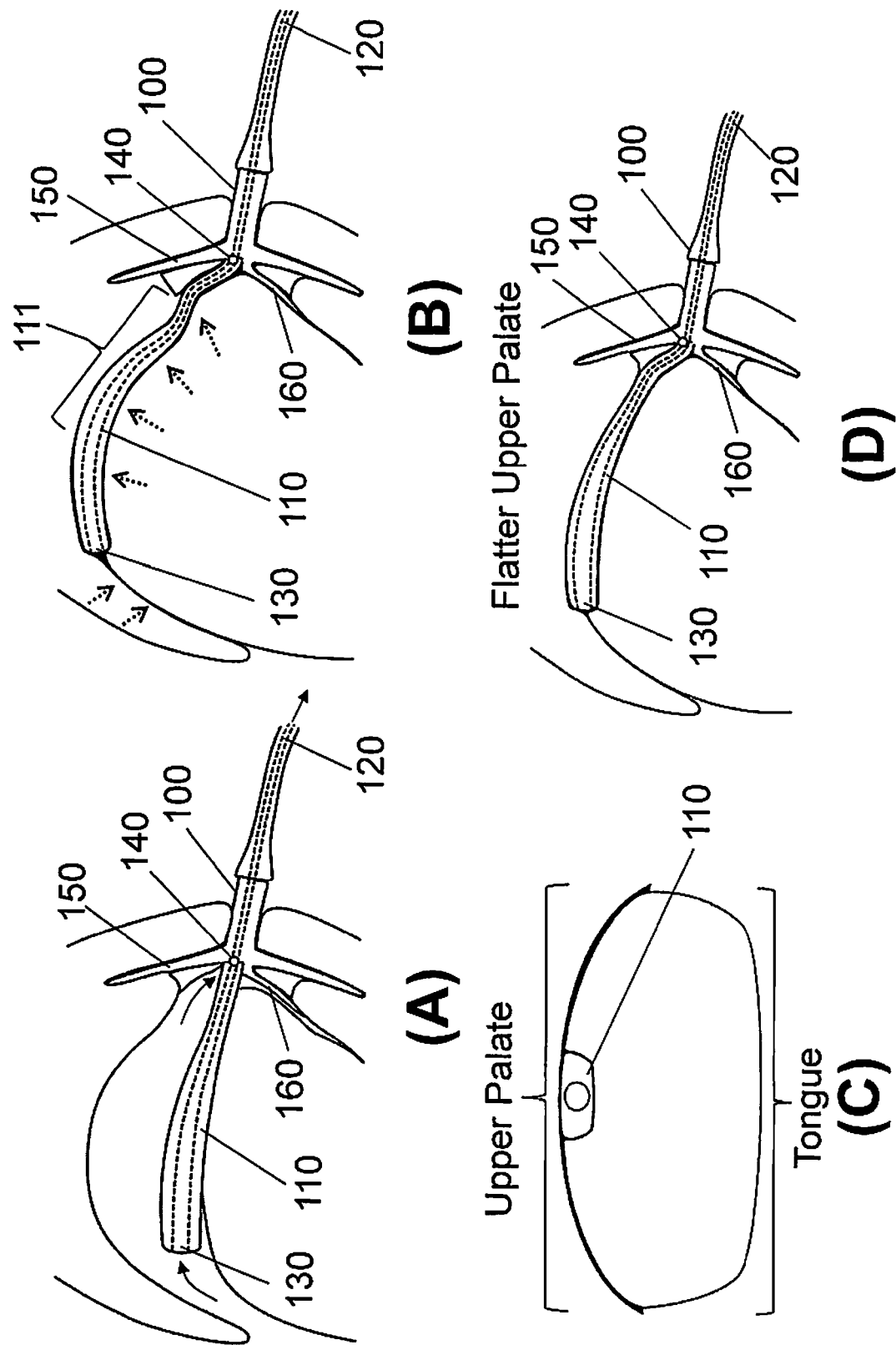

FIGS. 4A-C
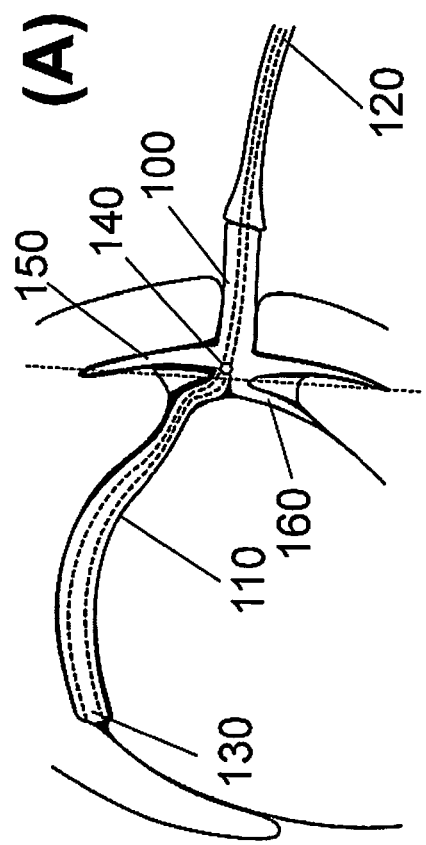
(A) Inline lower Jaw
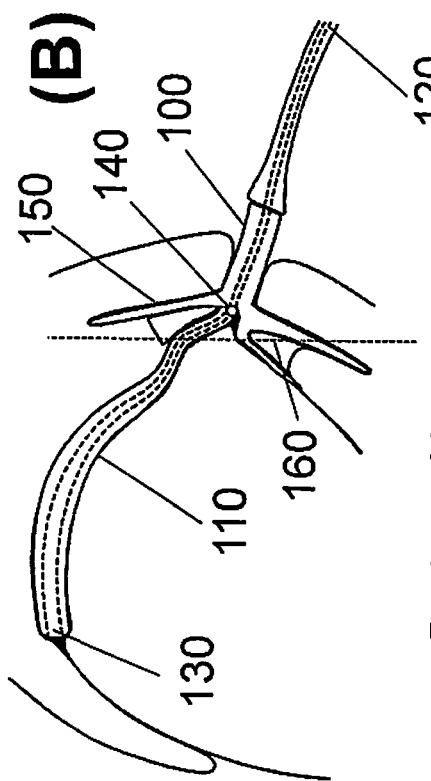
(B) Backward lower Jaw
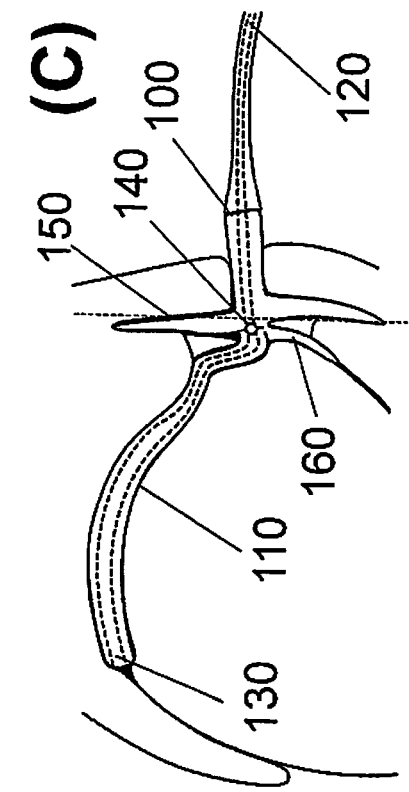
(C) Forward lower Jaw

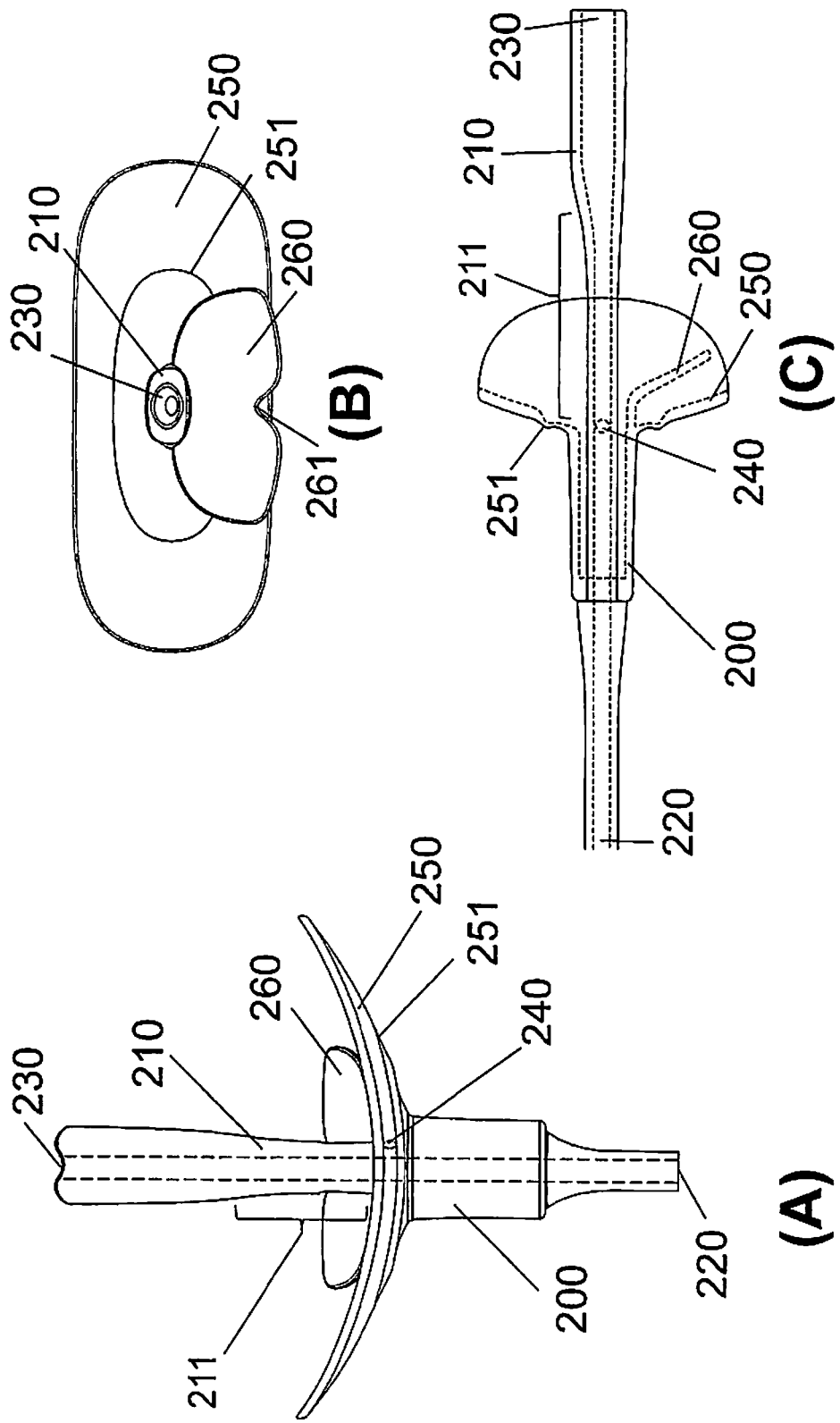
FIGS. 5A-C

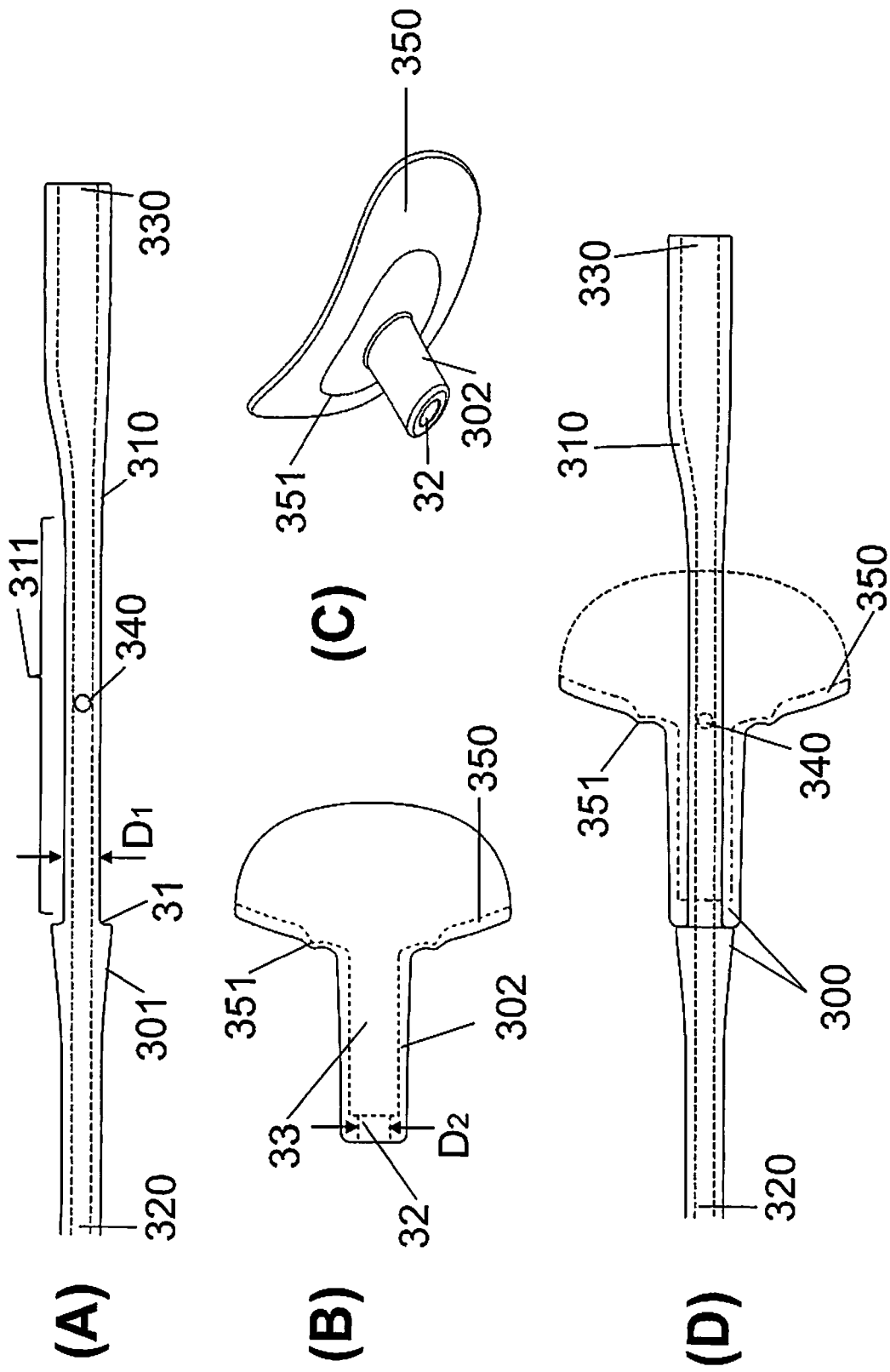
FIGS. 6A-D

FIGS. 7A-D
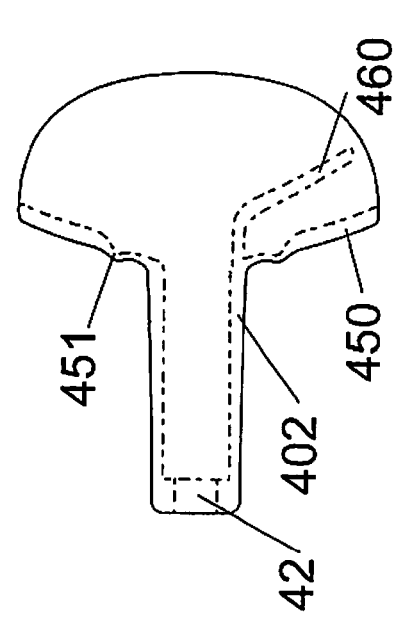
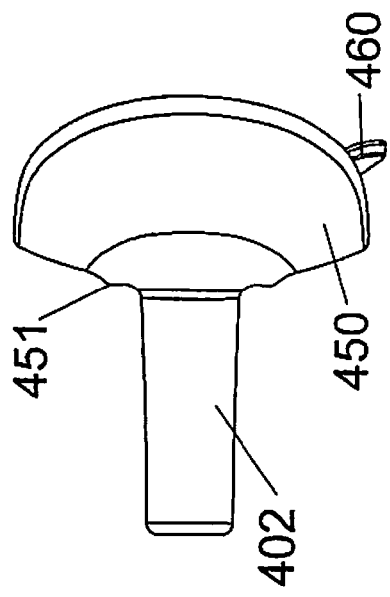
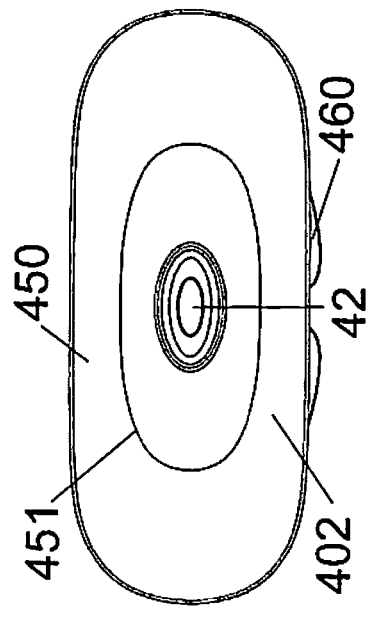
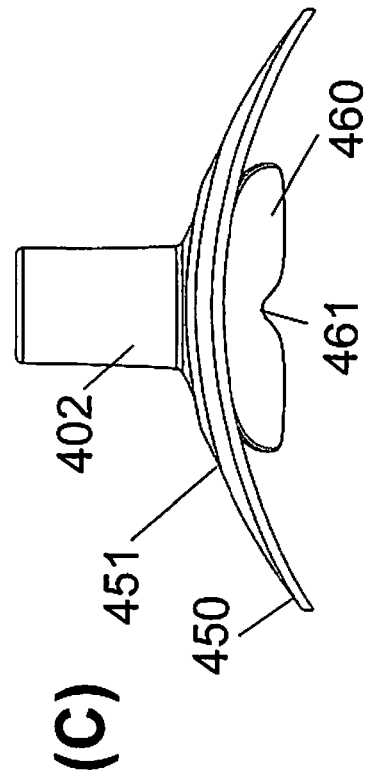

FIGS. 9A-B
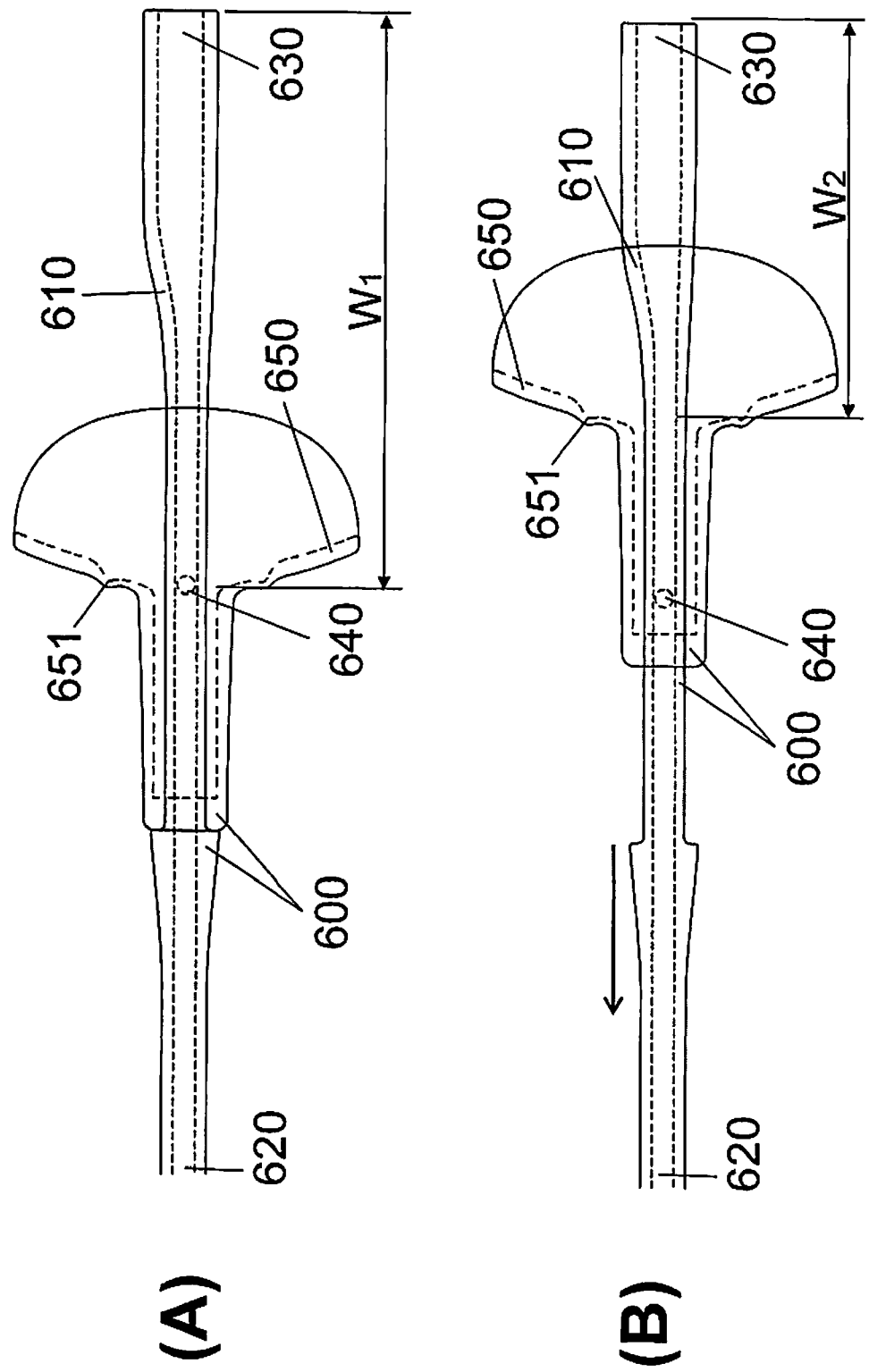

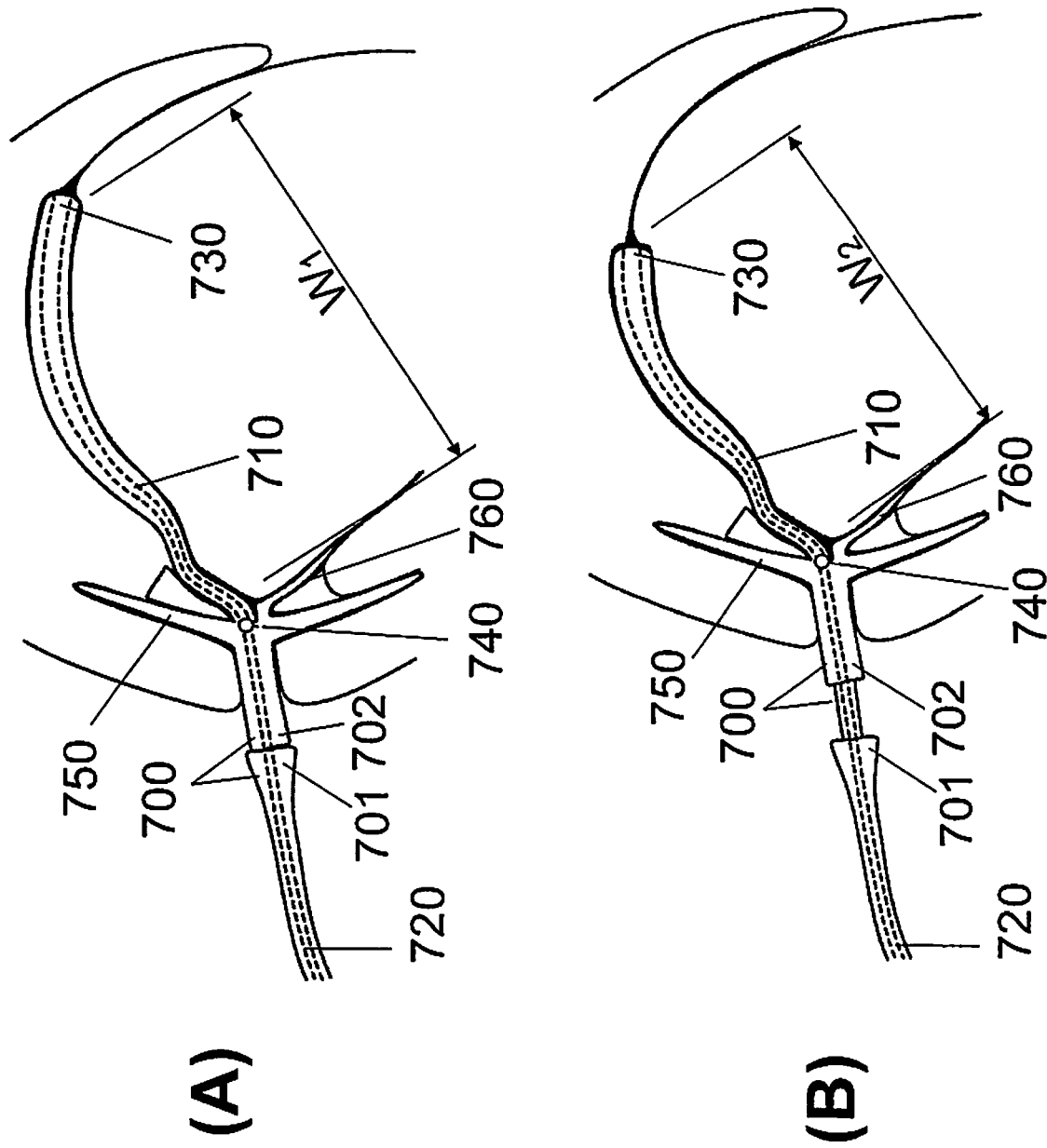
FIGS. 10A-B

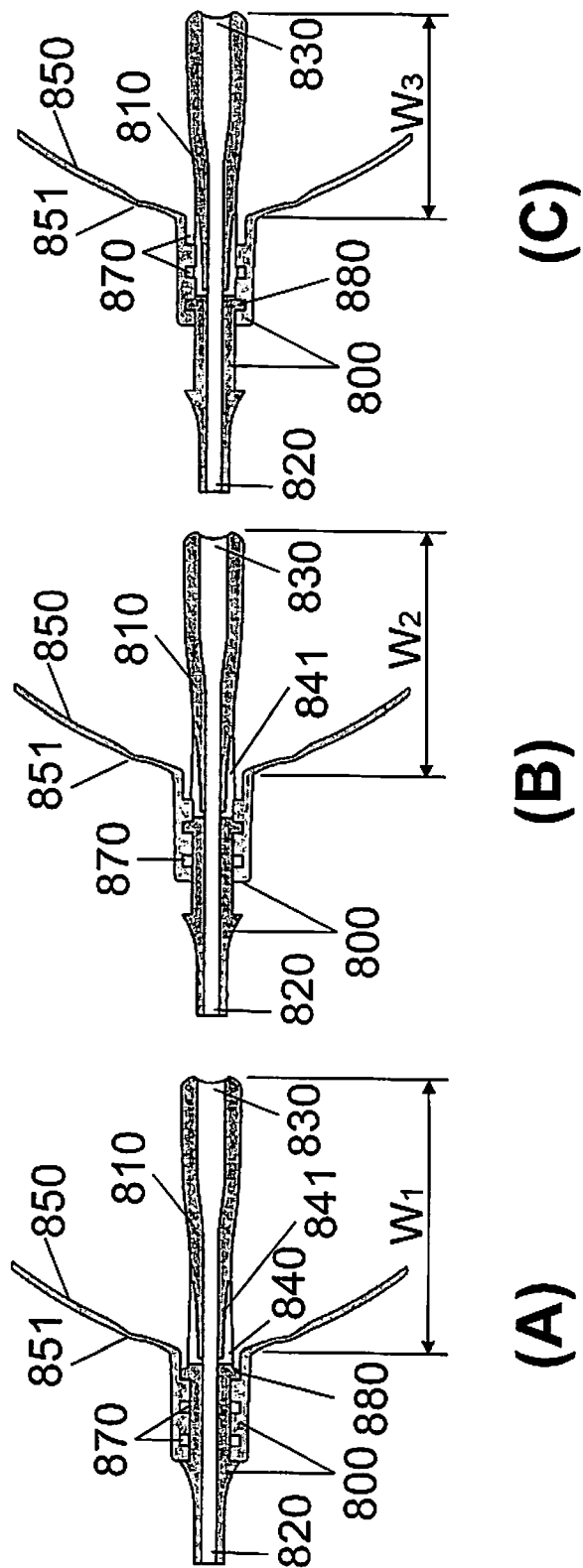
FIGS. 11A-C

FIGS. 12A-B
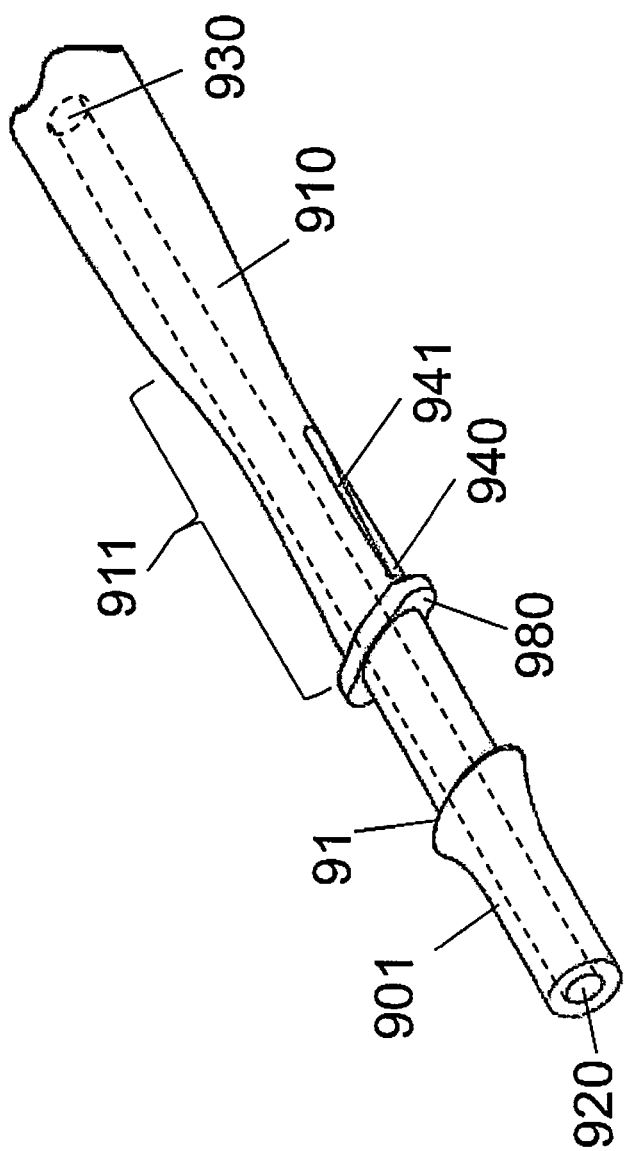
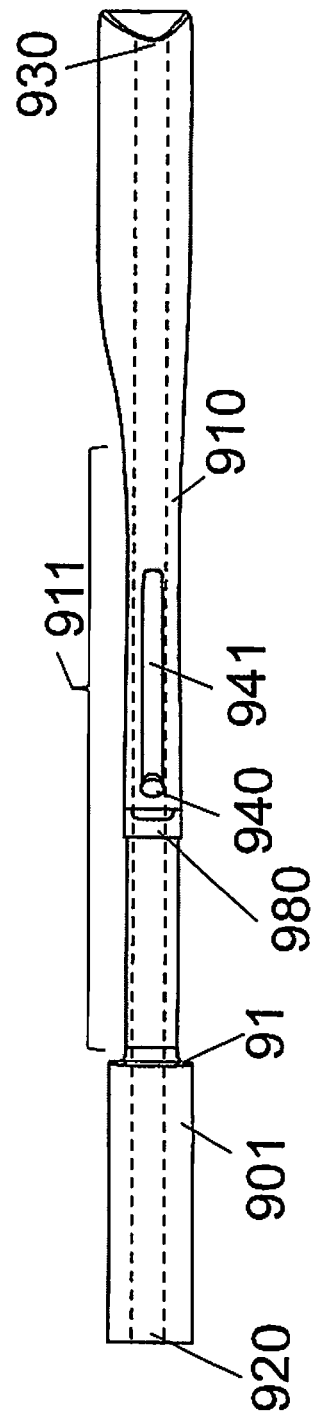

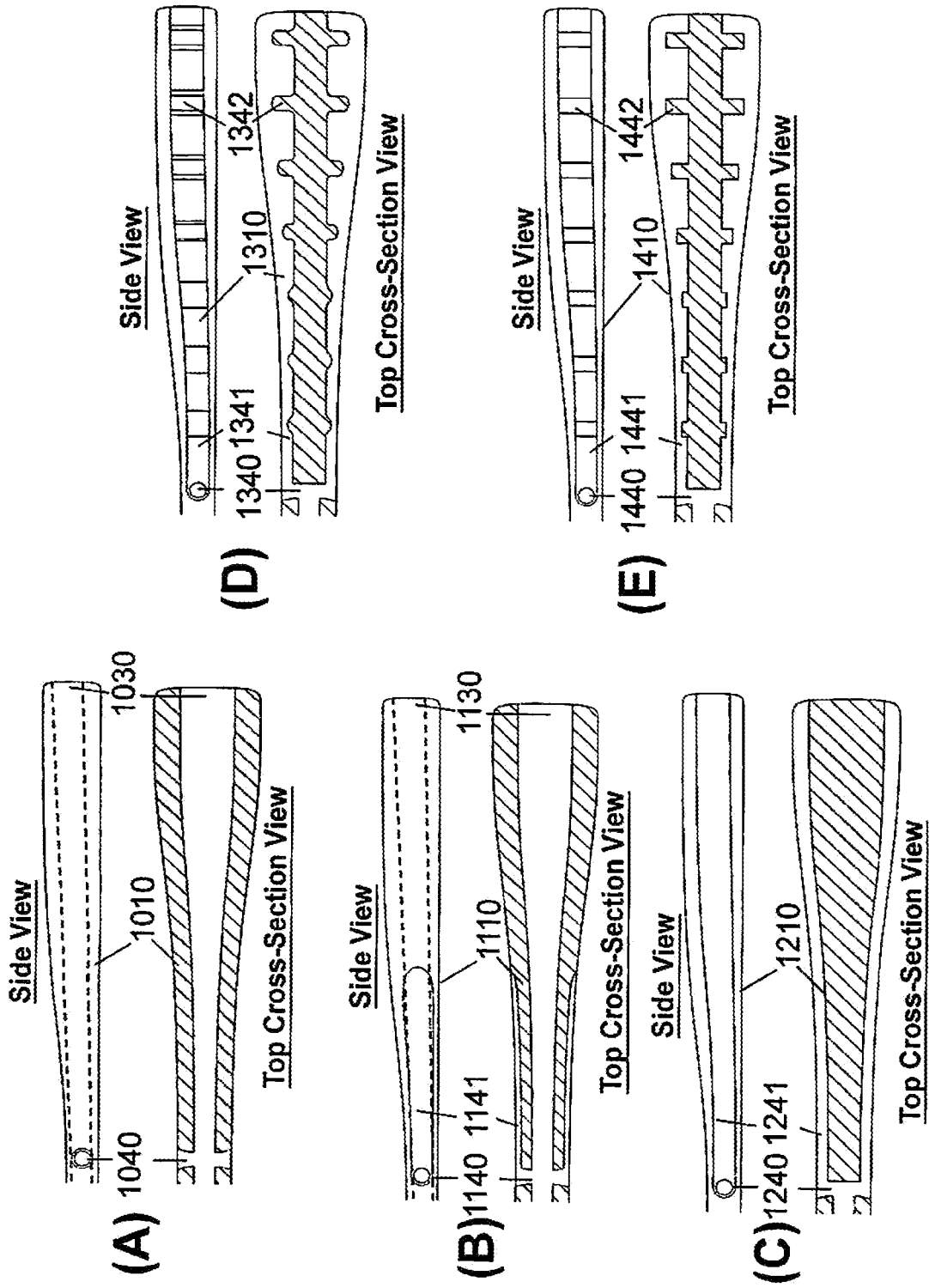
FIGS. 13A-E

FIGS. 14A-B
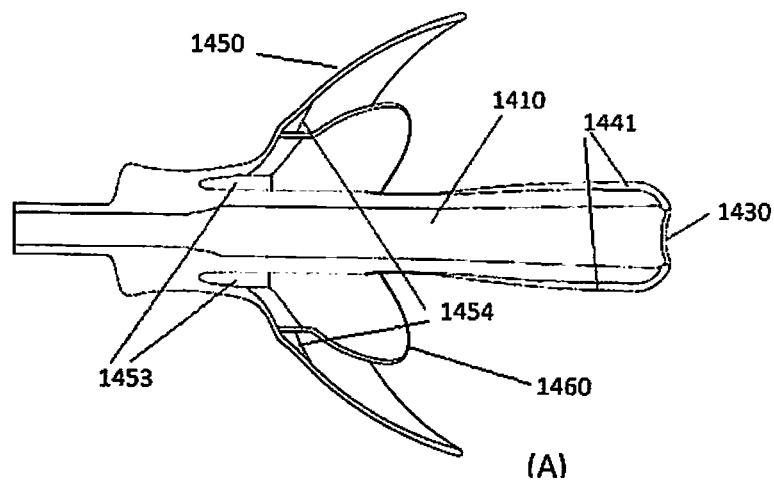
(A)
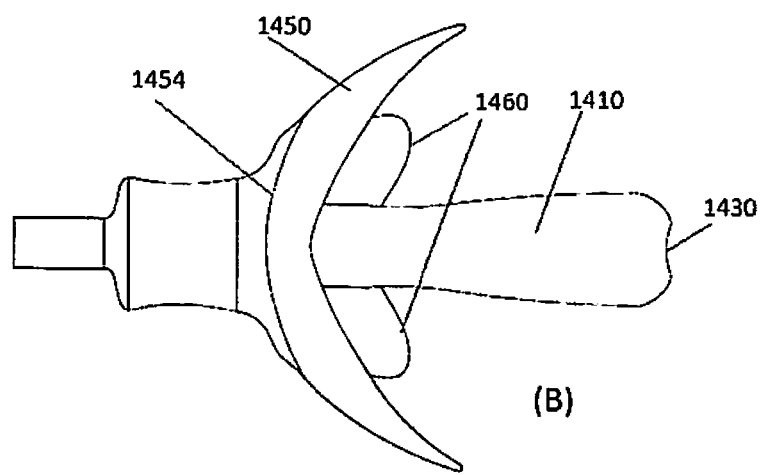
(B)

FIGS. 14C-E
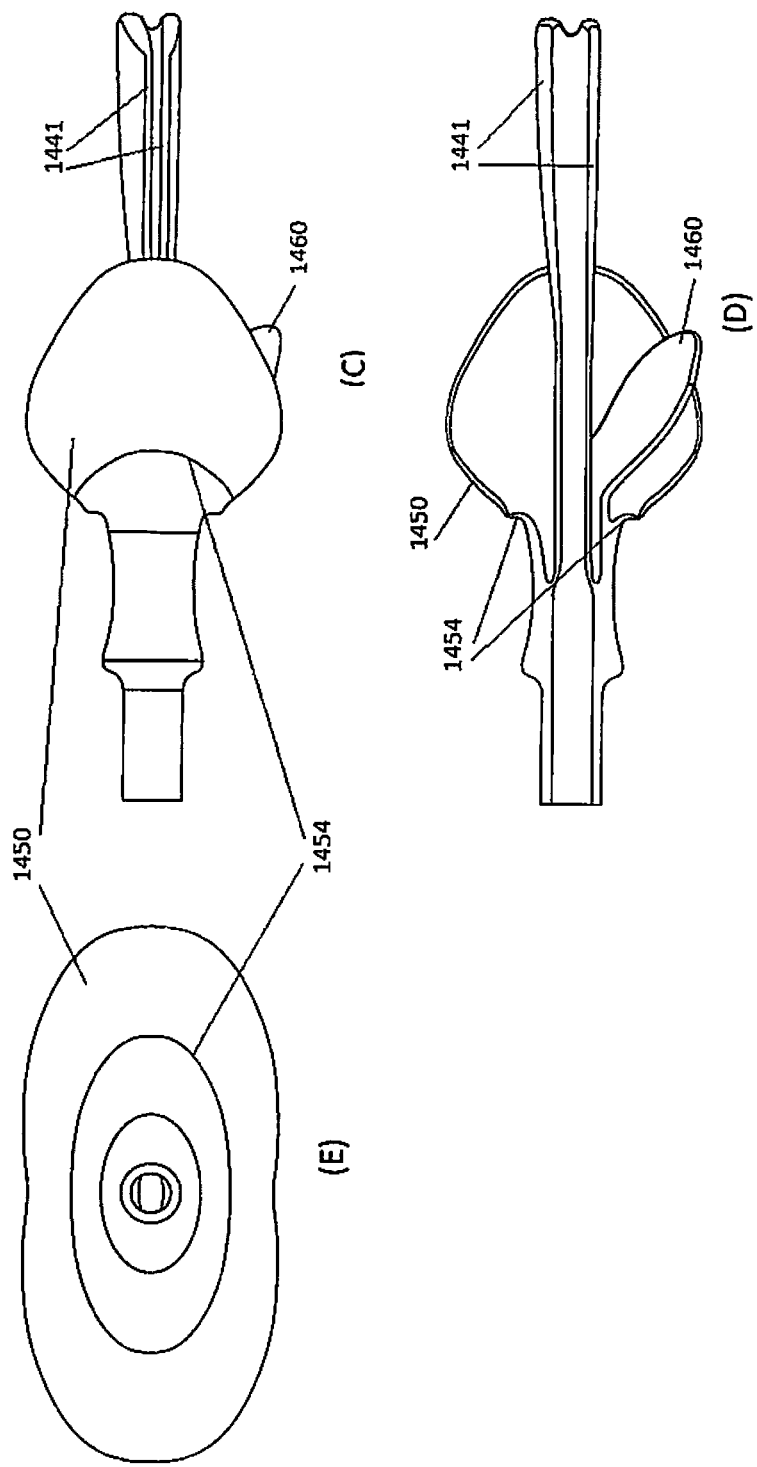

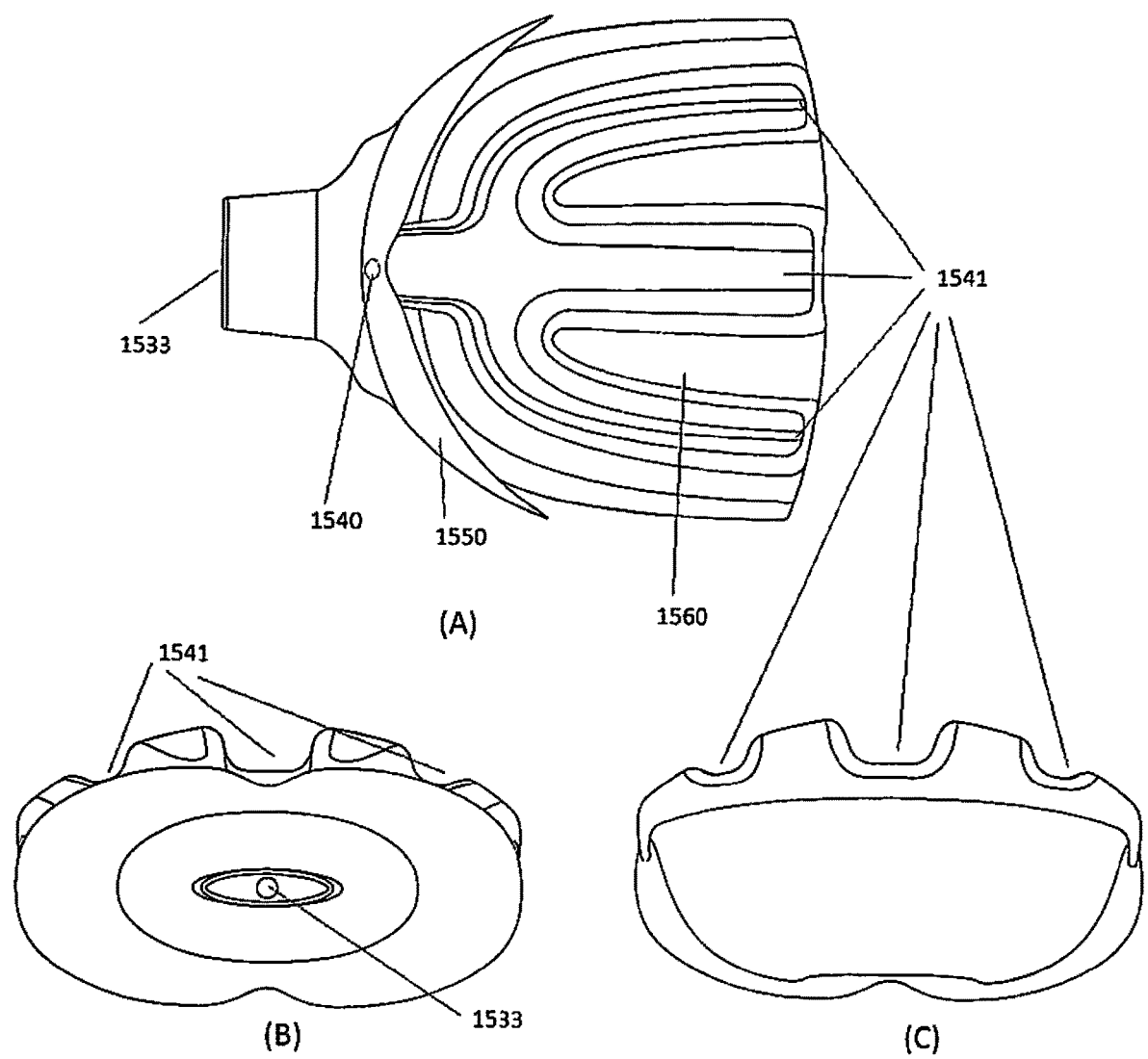
FIGS. 15A-C

FIGS. 15D-E
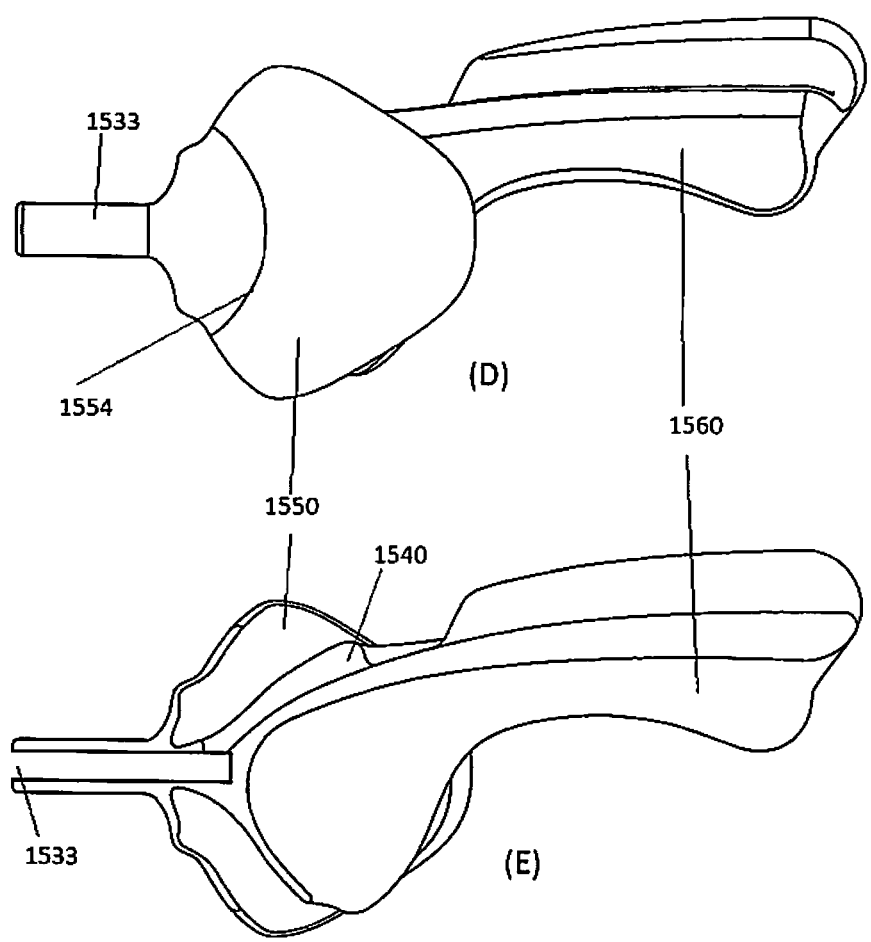

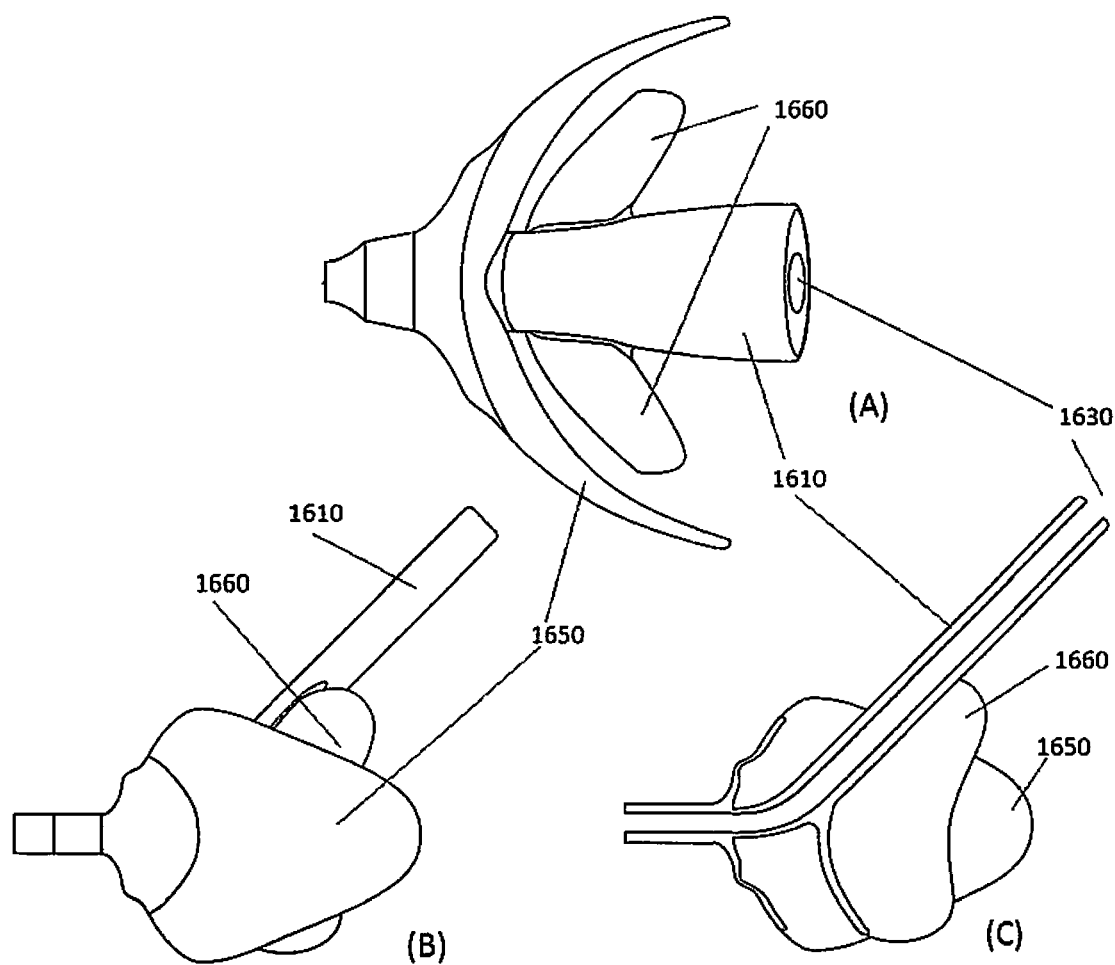

FIGS.16D-E
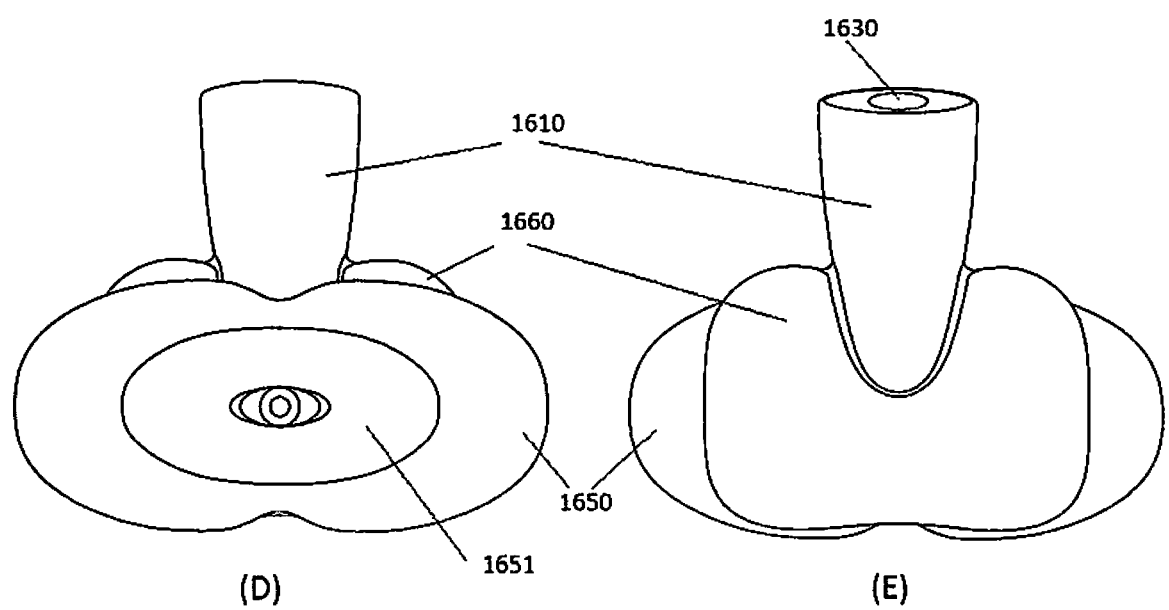

ORAL DEVICE TO ELIMINATE AIR SPACE IN ORAL CAVITY

CROSS-REFERENCE

The application claims the benefit of U.S. Provisional Application Ser. No. 61/751,559, filed on Jan. 11, 2013, which application is incorporated herein by reference.

BACKGROUND OF THE INVENTION

Obstructive sleep apnea (OSA), hypopnea, and upper airway resistance syndrome (UARS) are among a variety of known disorders characterized by episodes of complete or partial upper airway obstruction during such as sleep, anesthetization, or post anesthesia. OSA, hypopnea, and UARS cause intermittent interruption of ventilation during sleep with the consequence of potentially severe oxyhemoglobin desaturation. Typically, those afflicted with OSA, hypopnea, and/or UARS experience repeated, frequent arousal from sleep in response to the oxygen deprivation. The arousals result in sleep fragmentation and poor sleep continuity.

SUMMARY OF THE INVENTION

In one aspect provides herein an oral device for eliminating air space in oral cavity comprising a shield situated between lips and front teeth, a tube passing through the shield, and a negative pressure deliverable part connected to the shield or the tube, wherein the negative pressure deliverable part is situated at the space between tongue and upper palate conformable to the contour of the upper palate, whereby the oral device delivers negative pressure via the negative pressure deliverable part to the oral cavity to eliminate air space between the tongue and the upper palate.

In some embodiments, the shield is flexible. In some embodiments, the shield comprises a bendable structure which is conformable to the shape of front teeth and lips. In some embodiments, the shield further functions as a seal. In some embodiments, the shield further comprises at least one air vent. In some embodiments, the at least one air vent is in place at positions that allow the lips cover the air vent. In certain embodiments, the air vent comprises a one-way vale. In certain embodiments, the flexible tube comprises 1-20 middle openings. In certain embodiments, the flexible tube comprises two middle openings.

In some embodiments, the negative pressure deliverable part comprises a flexible tube. In some embodiments, the flexible tube comprises an anterior end to connect to a vacuum source. In certain embodiments, the vacuum source is delivered by a negative control system. In some embodiments, the flexible tube comprises a bendable middle part, which is conformable to the contours of the upper palate and the tongue. In some embodiments, the middle part is thinner than the rest part of the tube. In some embodiments, the flexible tube has a wider structure near the posterior end to provide rigidity of the tube. In certain embodiments, the wider structure near the posterior end has a curved edge. In some embodiments, the oral device further comprises a tongue protector to prevent direct impingement of teeth on the tip of the tongue. In certain embodiments, the tongue protector is disposed between the bottom of the tongue tip and the back side of the lower front teeth. In certain embodiments, the tongue protector further comprises an indentation to accommodate the shape of tongue frenulum.

In some embodiments, the flexible tube and the shield are detachable. In some embodiments, the detachable shield part has an inner chamber to accommodate part of a bendable middle part of the detachable flexible tube part. In certain embodiments, the detachable tube part has an outer surface which contacts with an inner surface of the detachable shield part to form a sealing interface to maintain negative pressure environment within oral cavity. In certain embodiments, the detachable tube part and detachable shield part have different sizes and are interchangeable to accommodate different anatomy of patients. In some embodiments, the flexible tube is slidable. In certain embodiments, the oral device further comprises a shield with multiple anchor stops in different positions. In certain embodiments, the flexible tube further comprises open channels along the flexible tube. In some embodiments, the number of open channels is corresponding to the number of middle openings on the flexible tube. In certain embodiments, the flexible tube comprises two open channels on the flexible tube.

In some embodiments, the flexible tube comprises a bendable middle part. In some embodiments, the bendable middle part is thinner than the rest part of the tube. In some embodiments, the tube has a wider structure than the rest of the tube near the posterior end. In certain embodiments, the structure near the posterior end has a curved edge. In certain embodiments, the open channels are extended to the posterior end of the flexible tubes. In certain embodiments, the section of the flexible tube having said open channels is solid. In certain embodiments, the flexible tube further comprises 1 to 20, 1 to 15, 1 to 10, or 1 to 7 supports to support the open channel from collapsing during the application of negative pressure.

In some embodiments, the negative pressure deliverable part comprises an extended tongue protector conformable the contour of the upper palate and is connected to the shield. In some embodiments, the extended tongue protector comprises at least one open channel. In some embodiments, the extended tongue protector is pre-shaped to conform the shape of upper palate. In some embodiments, the at least one open channel is connected to the at least one middle opening. In some embodiments, the tongue protector is integrated on the negative pressure deliverable part.

In another aspect provides herein an oral device for eliminating air space in oral cavity comprising a shield to be situated between lips and front teeth, and a tube passing through the shield, wherein the tube comprises a flexible negative pressure deliverable part to be situated at the space between tongue and upper palate conformable to the contour of the upper palate, whereby the oral device delivers negative pressure via the negative pressure deliverable part to the oral cavity to eliminate air space between the tongue and the upper palate. In some embodiments, the flexible negative pressure deliverable part further comprises at least one open channel along the flexible negative pressure deliverable part whereby the oral device delivers negative pressure via the negative pressure deliverable part and the at least one open channel to front and back of the oral cavity to eliminate air space between the tongue and the upper palate. In some embodiments, the shield has fold lines allowing the shield to be pliable and compliant to the tooth orientations and shapes. In some embodiments, the shield has recesses near the joint where the tube passing through allowing the tube to bend freely.

In another aspect provided herein are systems for eliminating air space in oral cavity comprising the invention oral device and a negative pressure control system providing a vacuum source. In some embodiments, the shield is flexible. In some embodiments, the shield comprises a bendable structure which is conformable to the shape of front teeth and lips. In some embodiments, the shield further functions as a seal. In some embodiments, the shield further comprises at least one air vent. In some embodiments, the at least one air vent is in place at positions that allow the lips cover the air vent. In certain embodiments, the air vent comprises a one-way vale. In certain embodiments, the flexible tube comprises 1-20 middle openings. In certain embodiments, the flexible tube comprises two middle openings. In some embodiments, the negative pressure deliverable part comprises a flexible tube. In some embodiments, the flexible tube comprises an anterior end to connect to a vacuum source. In certain embodiments, the vacuum source is delivered by a negative control system. In some embodiments, the flexible tube comprises a bendable middle part, which is conformable to the contours of the upper palate and the tongue. In some embodiments, the middle part is thinner than the rest part of the tube. In some embodiments, the flexible tube has a wider structure near the posterior end to provide rigidity of the tube. In certain embodiments, the wider structure near the posterior end has a curved edge. In some embodiments, the oral device further comprises a tongue protector to prevent direct impingement of teeth on the tip of the tongue. In certain embodiments, the tongue protector is disposed between the bottom of the tongue tip and the back side of the lower front teeth. In certain embodiments, the tongue protector further comprises an indentation to accommodate the shape of tongue frenulum. In some embodiments, the flexible tube and the shield are detachable. In some embodiments, the detachable shield part has an inner chamber to accommodate part of a bendable middle part of the detachable flexible tube part. In certain embodiments, the detachable tube part has an outer surface which contacts with an inner surface of the detachable shield part to form a sealing interface to maintain negative pressure environment within oral cavity. In certain embodiments, the detachable tube part and detachable shield part have different sizes and are interchangeable to accommodate different anatomy of patients. In some embodiments, the flexible tube is slidable. In certain embodiments, the oral device further comprises a shield with multiple anchor stops in different positions. In certain embodiments, the flexible tube further comprises open channels along the flexible tube. In some embodiments, the number of open channels is corresponding to the number of middle openings on the flexible tube. In certain embodiments, the flexible tube comprises two open channels on the flexible tube. In some embodiments, the flexible tube comprises a bendable middle part. In some embodiments, the bendable middle part is thinner than the rest part of the tube. In some embodiments, the tube has a wider structure than the rest of the tube near the posterior end. In certain embodiments, the structure near the posterior end has a curved edge. In certain embodiments, the open channels are extended to the posterior end of the flexible tubes. In certain embodiments, the section of the flexible tube having said open channels is solid. In certain embodiments, the flexible tube further comprises 1 to 20, 1 to 15, 1 to 10, or 1 to 7 supports to support the open channel from collapsing during the application of negative pressure. In some embodiments, the negative pressure deliverable part comprises an extended tongue protector conformable the contour of the upper palate and is connected to the shield. In some embodiments, the extended tongue protector comprises at least one open channel. In some embodiments, the extended tongue protector is pre-shaped to conform the shape of upper palate. In some embodiments, the at least one open channel is connected to the at least one middle opening. In some embodiments, the tongue protector is integrated on the negative pressure deliverable part.

In another aspect provided herein are methods for eliminating air space in oral cavity comprising attaching the invention oral device to the mouth of a patient; and applying a negative pressure by a negative control system on the middle openings and/or the posterior end of the flexible tube to both front and back of the oral cavity of the patient to eliminate air space between the tongue and the upper palate. In some embodiments, the shield is flexible. In some embodiments, the shield comprises a bendable structure which is conformable to the shape of front teeth and lips. In some embodiments, the shield further functions as a seal. In some embodiments, the shield further comprises at least one air vent. In some embodiments, the at least one air vent is in place at positions that allow the lips cover the air vent. In certain embodiments, the air vent comprises a one-way vale. In certain embodiments, the flexible tube comprises 1-20 middle openings. In certain embodiments, the flexible tube comprises two middle openings. In some embodiments, the negative pressure deliverable part comprises a flexible tube. In some embodiments, the flexible tube comprises an anterior end to connect to a vacuum source. In certain embodiments, the vacuum source is delivered by a negative control system. In some embodiments, the flexible tube comprises a bendable middle part, which is conformable to the contours of the upper palate and the tongue. In some embodiments, the middle part is thinner than the rest part of the tube. In some embodiments, the flexible tube has a wider structure near the posterior end to provide rigidity of the tube. In certain embodiments, the wider structure near the posterior end has a curved edge. In some embodiments, the oral device further comprises a tongue protector to prevent direct impingement of teeth on the tip of the tongue. In certain embodiments, the tongue protector is disposed between the bottom of the tongue tip and the back side of the lower front teeth. In certain embodiments, the tongue protector further comprises an indentation to accommodate the shape of tongue frenulum. In some embodiments, the flexible tube and the shield are detachable. In some embodiments, the detachable shield part has an inner chamber to accommodate part of a bendable middle part of the detachable flexible tube part. In certain embodiments, the detachable tube part has an outer surface which contacts with an inner surface of the detachable shield part to form a sealing interface to maintain negative pressure environment within oral cavity. In certain embodiments, the detachable tube part and detachable shield part have different sizes and are interchangeable to accommodate different anatomy of patients. In some embodiments, the flexible tube is slidable. In certain embodiments, the oral device further comprises a shield with multiple anchor stops in different positions. In certain embodiments, the flexible tube further comprises open channels along the flexible tube. In some embodiments, the number of open channels is corresponding to the number of middle openings on the flexible tube. In certain embodiments, the flexible tube comprises two open channels on the flexible tube. In some embodiments, the flexible tube comprises a bendable middle part. In some embodiments, the bendable middle part is thinner than the rest part of the tube. In some embodiments, the tube has a wider structure than the rest of the tube near the posterior end. In certain embodiments, the structure near the posterior end has a curved edge. In certain embodiments, the open channels are extended to the posterior end of the flexible tubes. In certain embodiments, the section of the flexible tube having said open channels is solid. In certain embodiments, the flexible tube further comprises 1 to 20, 1 to 15, 1 to 10, or 1 to 7 supports to support the open channel from collapsing during the application of negative pressure. In some embodiments, the negative pressure deliverable part comprises an extended tongue protector conformable the contour of the upper palate and is connected to the shield. In some embodiments, the extended tongue protector comprises at least one open channel. In some embodiments, the extended tongue protector is pre-shaped to conform the shape of upper palate. In some embodiments, the at least one open channel is connected to the at least one middle opening. In some embodiments, the tongue protector is integrated on the negative pressure deliverable part.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A and 2B show isometric and top views, respectively, of an exemplary oral device having a flexible tube conformable to the contour of the upper palate to eliminate air space in a patient's oral cavity during sleep.

FIGS. 3A-3D illustrate another aspect of the present invention showing various views of an exemplary oral device. FIGS. 3A and 3B show side views of an oral device having a flexible tube without and with negative pressure applied, respectively. FIG. 3C shows front cross-section view of an oral device having a flexible tube conformable to the contour of the upper palate with air space between tongue and soft palate eliminated. FIG. 3D shows side view of an oral device having a flexible tube conformable to a flatter upper palate with air space between tongue and soft palate eliminated.

FIGS. 4A-4C show side view of an exemplary oral device having a flexible shield conformable to inline, backward, and forward lower jaws, respectively, with air space between tongue and soft palate eliminated.

FIGS. 5A-5C illustrate another aspect of the present invention showing top, back, and side cross-section views, respectively, of an oral device having a flexible tube and a shield.

FIGS. 6A to 6D show various views of an exemplary oral device having a detachable flexible tube and a detachable shield.

FIGS. 7A to 7D illustrate another aspect of the present invention showing various views of an exemplary detachable flexible shield with a tongue protector.

FIGS. 9A and 9B show side cross-section views of an oral device having a slidable flexible tube in original position and forward position, respectively.

FIGS. 10A and 10B show side cross-section views of an oral device having a slidable flexible tube in original position and forward position, respectively, with air space between tongue and soft palate eliminated.

FIGS. 11A-11C show side cross-section views of an oral device having a slidable flexible tube with anchor points in different positions.

FIGS. 12A and 12B show different views of a detachable flexible tube with open channels.

FIGS. 13A-13E show variations of flexible tubes including tubes without opening at the posterior end with various open channels.

FIGS. 14A to 14F illustrate another aspect of the present invention showing various views of an exemplary oral device comprising open channels connecting with the posterior end without middle openings to deliver negative pressure from posterior part to anterior part of oral cavity.

FIGS. 15A to 15E illustrate another aspect of the present invention showing various views of an exemplary oral device with extended tongue protector which combines the tongue protector described herein with the function of a flexible tube pre-shaped and conformable to the shape of the upper plate.

FIGS. 16A to 16E illustrate yet another aspect of the present invention showing various views of an exemplary oral device comprising a flexible tube and a tongue protector where the tongue protector is integrated on the flexible tube.

DETAILED DESCRIPTION OF THE INVENTION

Figure 1:
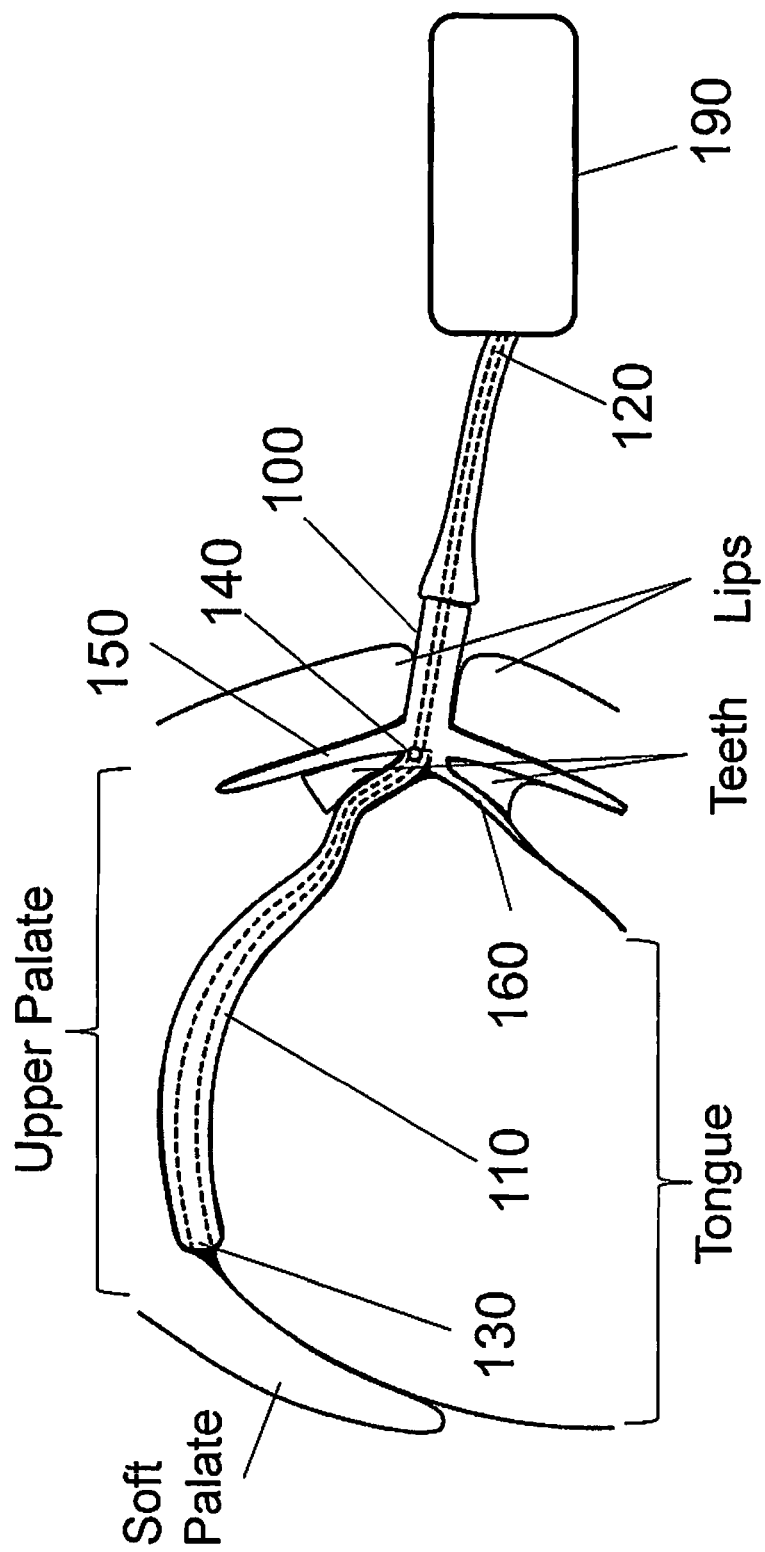
FIG. 1 illustrates one aspect of the present invention showing schematic diagrams of an exemplary system with an oral device comprising a negative pressure deliverable part (e.g., a flexible tube) conformable to the contour of the upper palate to eliminate air space in a patient's oral cavity during sleep.

Oral and external devices for treating sleep apnea and snoring have been disclosed in several publications utilizing several theories. It has been proposed to apply a negative pressure to the forward end of the patient's mouth, typically at or just behind the lips, to pull the tongue forward in order to lift the rear portion of the tongue away from the back of the airway. For example, an oral device for treatment of obstructive sleep disorders is characterized in that the tongue is protected and separated from the teeth when the device is in use. (See e.g., U.S. Pat. No. 4,304,227) The oral device further comprises a tongue shaped cavity for receiving the tongue where a negative pressure is applied directly on the soft tissues of the tongue to hold the tongue within the cavity. However, such negative pressure may cause damage to the soft tissues of the tongue.

Although various devices have been developed to facilitate breathing for those suffering from OSA, hypopnea or UARS by using oral negative pressure, to properly control negative pressure applied to oral cavity remains problematic.

The present invention provides devices and systems for properly controlling negative pressure applied to oral cavity, facilitating breathing and treating sleep apnea and snoring.

Reference will now be made in detail to the present exemplary embodiments, examples of which are illustrated in the accompanying drawings. Wherever possible, the same reference numbers are used in the drawings and the description to refer to the same or like parts.

Referring to FIG. 1, a schematic diagram of an exemplary invention system comprising a negative pressure control system 190 and an oral device 100 comprising a negative pressure deliverable part (e.g., a flexible tube 110), an optional tongue protector 160, and a shield 150 is shown. The oral device 100 for placement in a patient's oral cavity comprises a shield 150 to be situated between lips and front teeth, where a tube 110 passes through the shield is connected to a portion flexible and conformable to the contour of the upper palate (i.e., a negative pressure deliverable part). The flexible tube 110 has an anterior end 120 connected the negative pressure control system 190 which provides a vacuum source and a posterior end 130 to be situated between tongue and upper palate. The flexible tube 110 further optionally has at least one middle opening 140 near the shield 150. In some embodiments, the flexible tube 110 has 1 to 20, 1 to 15, 1 to 10, 1 to 5, 1 to 3, or 1 to 2 middle openings. As shown in FIG. 1, the position of the middle opening 140, in some embodiments, is on the side of the tube where it has less chance to be blocked by the soft tissue in patient's oral cavity. In certain embodiments, the flexible tube 110 has two middle openings 140 positioned on the side of the tube. The flexible tube 110 delivers negative pressure to both front and back of the oral cavity to eliminate air space between the tongue and the upper palate. An ordinary skilled in the art would readily apply the suitable negative pressure control system providing a vacuum source (e.g. by an electronic pump disclosed in US2009/0288660, which is incorporated herein by reference, or the like).

In some embodiments, the shield 150 also functions as a seal to facilitate proper control of negative pressure applied to oral cavity. An ordinary skilled in the art would readily appreciate that the proper control of negative pressure applied to oral cavity is achieved via the opening of the posterior end 130 and at least one middle opening 140 of the tube and optionally via the shield which functions as a seal.

FIGS. 2A and 2B further illustrate an exemplary oral device in accordance with FIG. 1. FIG. 2A illustrates an isometric view of an oral device 100 comprising a flexible tube 110 passing through a shield 150. In some embodiments, the shield 150 comprises a bendable structure 151, which is conformable to the shape of patient's front teeth and lips. In one embodiment, the bendable structure 151 is a fold line 1454, as described in more detail below. In certain embodiments, the flexible tube 110 has a bendable middle part 111, which is conformable to the contours of the upper palate and the tongue. In some embodiments, the middle part 111 is thinner than the rest part of the tube. The flexible tube 110 has an anterior end 120 to connect to a vacuum source (e.g., via a negative pressure control unit) and a posterior end 130 in place at the space between the tongue and the upper palate. The optional middle opening 140 is shown in FIG. 2A near the center of the shield 150. FIG. 2B illustrates a top view of an exemplary oral device in accordance with the embodiment shown in FIG. 1. The shield 150 is disposed between the front teeth and the lips and the flexible tube 110, in some embodiments, is disposed along the center line of the tongue. The flexible tube 110, in some embodiments, has a wider structure 131 near the posterior end 130 to provide rigidity of the tube, which prevent from collapsing due to being compressed by the tongue and the upper palate.

Referring to FIGS. 3A-3D, exemplary methods and system employing the present invention are described. FIG. 3A shows the side views of an exemplary oral device comprising a flexible tube without applying negative pressure. An oral device 100 is placed in a patient's oral cavity. The oral device 100 has a negative pressure deliverable part (i.e., a flexible tube 110) disposed between the tongue and the upper palate. The shield 150 is disposed between the front teeth and the lips. The anterior end 120 of the oral device 100 is connected to a vacuum source. The posterior end 130 and optionally at least one middle opening 140 of the oral device 100 is disposed between the tongue and upper palate and near the middle part of the shield 150, respectively. With negative pressure applied through the oral device, air space between the tongue and the upper palate is reduced gradually. An ordinary skilled in the art would readily appreciate that the tube 110 acting as a negative pressure deliverable part is flexible to conform to any contours of the upper palate of patients. FIG. 3B illustrates the tongue is drawn forward and upward (i.e., superior) to push and deform the flexible tube 110 to conform to the contour of the upper palate by application of negative pressure via the optionally at least one middle opening 140 and via posterior end 130 which further eliminates air space between the tongue and the soft palate. FIG. 3C shows front cross-section view of an oral device having a flexible tube conformable to the contour of the upper palate in accordance with FIG. 3B where air space between tongue and soft palate is reduced. The flexible tube 110 has a minimal cross section and occupies very little space in the oral cavity. FIG. 3D shows a side view of an oral device having a flexible tube conformable to a flatter upper palate (compared to one shown in FIG. 3(B)) with air space between tongue and soft palate eliminated. In some embodiments, the flexible tube 111 further comprises a more bendable part 111 (see FIG. 3 B) to accommodate different anatomy of upper palate of different patients. An ordinary skilled in the art would readily recognize that the bendable part 111 is not limited to the particular section shown in FIG. 3B, but any part that is conformable to the contour of the upper palate.

FIGS. 4A-4C illustrate a further variation of an oral device 100. FIG. 4A shows a side view of an oral device 100 comprising a flexible shield conformable to an inline lower jaw (in relative to upper jaw). The shield 150 is flexible and may further have a bendable structure (not shown), which can accommodate different anatomy of front teeth and lips of different patients, for patient with backward lower jaw (e.g., as shown in FIG. 4B) and forward lower jaw (e.g., as shown in FIG. 4C), respectively.

FIGS. 5A-5C illustrate another variation of invention oral devices showing top, back, and side cross-section views of an oral device 200 comprising a flexible tube 210 and a shield 250 where the flexible tube 210 passes through a shield 250. In some embodiments, the shield 250 has a bendable structure 251, which is conformable to the shape of front teeth and lips. The flexible tube 210, in some embodiments, further has a bendable middle part 211 (i.e., a negative pressure deliverable part), which is conformable to the contours of the upper palate and the tongue. Thus, in some embodiments, the tube passing through the shield is part of or directed connected to a flexible tube as described herein where the flexible tube functions as a negative pressure deliverable part. In certain embodiments, the middle part 211 is thinner than the rest part of the tube allowing more flexibility. In certain embodiments, the middle part 211 remains the same thickness as the rest part of the tube but still maintains the desired flexibility. An ordinary skilled in the art would readily realize it via the structure design (e.g., by a reinforced coating) or the material used (e.g., a more rigid produced material). In some embodiments, the material used to construct the middle part 211 is the same as the rest of the tube where the middle pat is thinner than the rest of the tube. In certain embodiments, the material used to construct the middle part 211 is not the same as the rest of the tube and provides more flexible characteristic. The flexible tube 210, in some embodiments, has a wider structure near the posterior end 230 to provide rigidity of the tube, which prevent from collapsing due to being compressed by the tongue and the upper palate. In certain embodiments, the wider structure near the posterior end 230 has a curved edge. The flexible tube 210 has an anterior end 220 to connect to a vacuum source and a posterior end 230 in place at the space between the tongue and the upper palate. The flexible tube 210 further optionally has at least one middle opening 240 near the center of the shield 250. In some embodiments, the flexible tube 210 is one piece from the anterior end 220 to the posterior end 230. In some embodiments, the flexible tube 210 connects to a tube passing through the shield. In some embodiments, the oral device 200 further has a tongue protector 260 to prevent direct impingement of teeth on the tip of the tongue. The tongue protector 260 is disposed between the bottom of the tongue tip and the back side of the lower front teeth. In certain embodiments, the tongue protect 260 further has an indentation 261 to accommodate the shape of tongue frenulum.

In some embodiments of the invention, there is provided an oral device 300 comprises a detachable tube part 301 and a detachable shield part 302 shown in various views in FIGS. 6A to 6D. FIG. 6A illustrates an exemplary detachable tube part 301 having a flexible tube 310 which is conformable to the contours of the upper palate and the tongue. In some embodiments, the flexible tube 310 comprises a bendable middle part 311. In certain embodiments, the middle part 311 is thinner than the rest part of the tube. In certain embodiments, the middle part 311 remains the same thickness as the rest part of the tube but still maintains the desired flexibility. An ordinary skilled in the art would readily recognize that to achieve the same flexibility by different thickness of the middle part 311, the material used, the shape, and/or the length of the middle part 311 need to be adjusted accordingly. The flexible tube 310, in some embodiments, has a wider structure near the posterior end 330 to provide rigidity of the tube, which prevent from collapsing due to being compressed by the tongue and the upper palate. In certain embodiments, the wider structure near the posterior end 330 has a curved edge. The flexible tube 310 has an anterior end 320 to connect to a vacuum source and a posterior end 330 in place at the space between the tongue and the upper palate. The flexible tube 310 further optionally has at least one middle opening 340 near the center of the shield 350 (see FIG. 6A and FIG. 6D). FIG. 6B illustrate a detachable shield part 302, having a shield 350 which comprises a bendable structure 351 being conformable to the shape of front teeth and the lips. The detachable shield part 302 has an inner chamber 33 (see FIG. 6B) to accommodate part of the bendable middle part 311 (see FIG. 6A) of the flexible tube 310. The detachable tube part 301 and detachable shield part 302 may have different sizes and are interchangeable to accommodate different anatomy of patients. In some embodiments, the detachable tube part 301 has an outer surface 31 (see FIG. 6A) which contacts with an inner surface 32 (see FIG. 6B/6C) of the detachable shield part 302 to form a sealing interface to maintain negative pressure environment within oral cavity. To ensure a good fit, the diameter of D1 should be corresponding to the diameter of D2. A complete assembly is shown in FIG. 6D.

FIGS. 7A to 7D illustrate another embodiment of the invention showing various views of a detachable shield part 402 with a tongue protector 460 where the tongue protector 460 is disposed between the bottom of the tongue tip and the back side of the lower front teeth. FIG. 7A/B show the side-cross views of a detachable shield part 402 comprising a bendable middle part 451, a shield 450 and a tongue protector 460. In some embodiments, the detachable shield part 402 further comprises an inner surface 42 to accommodate a detachable tube part to form a sealing interface (see FIGS. 7B and 7D). In certain embodiments, the tongue protect 460 further comprises an indentation 461 (e.g., see FIG. 6C) to accommodate the shape of tongue frenulum.

Figure 8:
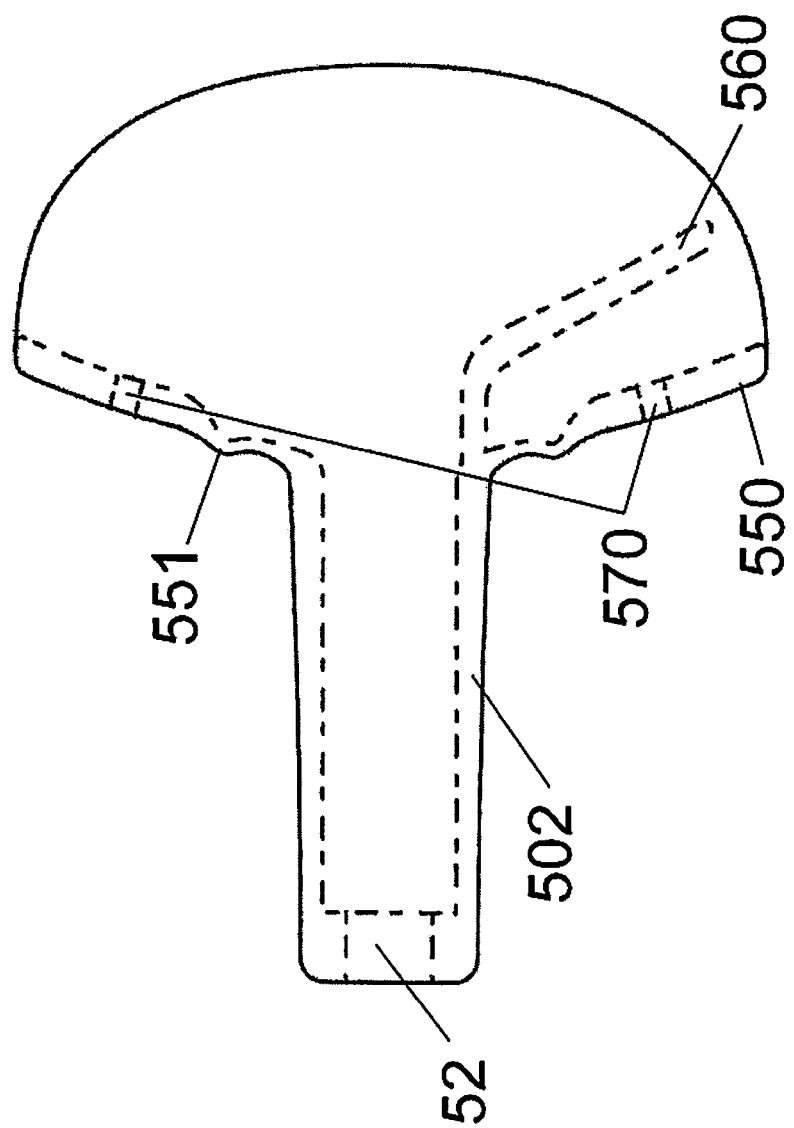
FIG. 8 illustrate another aspect of the present invention showing a side cross-section view of a detachable shield with air vents.
Figure 14F:
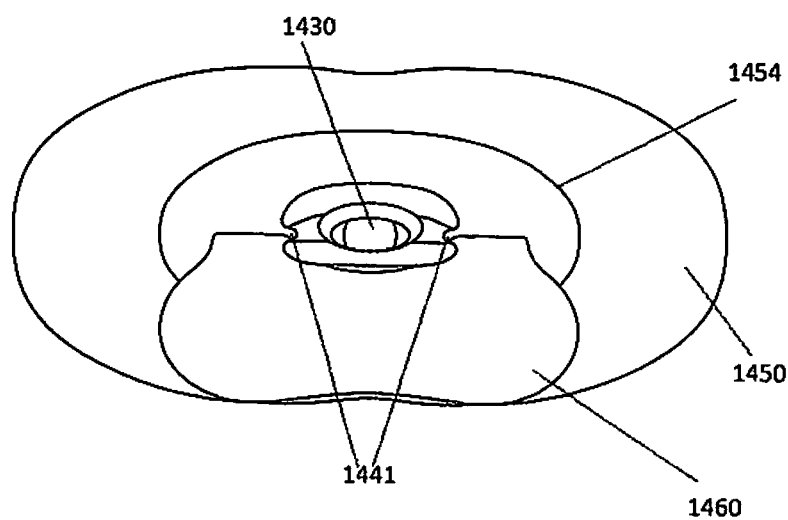

Referring to FIG. 8 shows the side cross-section view of a detachable shield part 502 comprising a tongue protector 560, a shield 550 and air vents 570 wherein the detachable shield part comprises a bendable middle part 551. The detachable shield part further comprises an inner surface 52 to accommodate a detachable tube part to form a sealing interface. The air vents 570 allow the patient to breathe more freely when the patient tries to open mouth or exhale through mouth. In some embodiments, the air vents comprise one-way vale to preserve the seal function of the detachable shield. A one-way vale restricts air entering from outside but allowing air to go out from the oral cavity. In some embodiments, the air vents are in place at positions that allow the lips to cover the air vents. For example, the air vents are positioned slightly above or below incisal face, where the air vents is in front of the upper front teeth or the bottom front teeth, and behind the lips.

Referring now to FIGS. 9A-9B, illustrate another aspect of the present invention showing an oral device 600 comprising a slidable flexible tube 610 in original position ($W_1$, FIG. 9A) and forward position ($W_2$, FIG. 9B), respectively. The oral device comprises a flexible tube 610 and a shield 650 comprising a bendable middle part 651 where the flexible tube 610 passes through the shield 650. The flexible tube 610 further optionally comprises at least one middle opening 640. The flexible tube 610 has an anterior end 620 to connect to a vacuum source and a posterior end 630 in place at the space between the tongue and the upper palate. The slidable flexible tube 610 allows a patient to adjust the position of the posterior end 630 to provide a more comfortable or effective location to deliver negative pressure between the tongue and the upper palate.

FIGS. 10A-10B show the side cross-section views of an oral device 700 comprising a slidable flexible tube 710 in original position (W1, FIG. 10A) and forward position (W2, FIG. 10B), respectively, with air space between tongue and soft palate eliminated. An oral device 700 is placed in a patient's oral cavity. The oral device 700 has a slidable flexible tube 710 disposed between the tongue and the upper palate. The shield 750 is disposed between the front teeth and the lips. The anterior end 720 of the oral device 700 is connected to a vacuum source (not shown). The posterior end 730 and at least one middle opening 740 of the oral device 700 is disposed between the tongue and upper palate and near the middle part of the shield 750, respectively. To accommodate the different anatomy of patients, the detachable tube part 701 can be moved away from the detachable shield part 702 which also move the position of the posterior end 730 forward. In certain embodiments, the posterior open end 730 is located anteriorly to the boundary between the hard palate and the soft palate, thus prevents the soft tissue on soft palate from blocking or being sucked into the posterior open end 730. The oral device 700 can further have a tongue protector 760 to prevent direct impingement of teeth on the tip of the tongue.

Referring now to FIGS. 11A to 11C, illustrate another aspect the present invention where an oral device 800 comprises a slidable flexible tube 810 with anchor points 880 in different positions. The oral device 800 further comprises a shield 850 with multiple anchor stops 870, which allow a patient to adjust the slide tube 810 to distinct positions (e.g., at $W_1$, $W_2$, $W_3$). The oral device comprises a slidable flexible tube 810 and a shield 850 comprising a bendable middle part 851 where the flexible tube 810 passes through the shield 850. The flexible tube 810 further comprises at least one middle opening 840. The flexible tube 810 has an anterior end 820 to connect to a vacuum source and a posterior end 830 in place at the space between the tongue and the upper palate. The slidable flexible tube 810 allows a patient to adjust the position of the posterior end 830 to distinct positions (e.g., at $W_1$, $W_2$, $W_3$) with anchor points 880 in different positions to provide a more comfortable or effective location to deliver negative pressure between the tongue and the upper palate. The flexible tube 810, in some embodiments, further comprises open channels 841 (e.g., shown at both sides of the flexible tube). The open channels 841 along the flexible tube 810 allow negative pressure distribution and prevent the middle opening 840 from obstruction by the soft tissue or tongue.

Referring to FIGS. 12A-12B, different views of a detachable tube part 901 having flexible tube 910 with open channels 941 will be described. In some embodiments, the flexible tube 910 comprises a bendable middle part 911. In certain embodiments, the middle part 911 is thinner than the rest part of the tube. In certain embodiments, the middle part 911 remains the same thickness as the rest part of the tube but still maintains the desired flexibility. The flexible tube 910 has an anterior end 920 to connect to a vacuum source and a posterior end 930 in place at the space between the tongue and the upper palate. The flexible tube 910, in some embodiments, has a wider structure near the posterior end 930 to provide rigidity of the tube, which prevent from collapsing due to being compressed by the tongue and the upper palate. In some embodiments, the posterior end 930 has a curved edge which decreases the risk of complete blockage by the soft tissue or tongue. The flexible tube 910 further comprises at least one middle opening 940 near an anchor stop 980. In some embodiments, the detachable tube part 901 has an outer surface 91 (see FIG. 12A) which contacts with an inner surface of the detachable shield part to form a sealing interface to maintain negative pressure environment within oral cavity. The open channels 941 are disposed along opposite sides of the flexible tube 910 between upper and lower surfaces of the tube. Each open channel 941 defines a groove having a length extending along the length of the tube 910 and a depth extending laterally inward from one of the sides of the tube. The open channels 941 are in fluid communication with the middle openings 940 to allow negative pressure distribution and prevent the middle opening 940 from obstruction by the soft tissue or tongue. In some embodiments, the flexible tube 910 comprises at least one open channel, two open channels, three open channels, four open channels or more. The number of open channels is corresponding to the number of middle openings on the flexible tube. In certain embodiments, the flexible tube 910 comprises two open channels 940 connecting the middle openings 940 on two sides of flexible tube 910.

Referring to FIG. 13A, a flexible tube 1010 comprising at least one middle opening 1040 is shown in side view and top cross-section view. FIGS. 13B-13E further illustrate various embodiments of the present invention showing flexible tubes 1110 (FIG. 13B), 1210 (FIG. 13C), 1310 (FIG. 13D) and 1410 (FIG. 13E), with various designs of open channels 1141, 1241, 1341 and 1441, respectively. The open channels along the flexible tube allow negative pressure distribution and prevent the middle openings 1140, 1240, 1340 and 1440 from obstruction by the soft tissue or tongue. FIG. 13B shows that the open channel 1141 is located within the limitation of bendable part and does not extend to the posterior end. In certain embodiments, the open channels are extended to the posterior end of the flexible tubes (see e.g., the open channels 1241, 1341 and 1441 extended to the posterior end of the flexible tubes 1210, 1310 and 1410) where these sections of the flexible tube are solid, and therefore replace the function of the posterior end (1030 and 1130) to deliver negative pressure between tongue and upper palate (see e.g., FIGS. 13C to 13E). In some embodiments, as illustrated in FIG. 13D and 13E, the flexible tube further comprises several supports 1342 or 1442 within the flexible tube to support the open channel from collapsing during the application of negative pressure. As shown in FIGS. 13D and 13E the supports 1342, 1442 are integral with the flexible tube 1310, 1410. The supports 1342, 1442 are positioned in the open channel 1341, 1441 and extend between the top and bottom of the open channel. In some embodiments, the flexible tube comprises 1 to 20, 1 to 15, 1 to 10, 1 to 7, 1 to 6, 1 to 5, 1 to 4, 1 to 2, or one support(s). The size and the position of the supports depend on the length of the open channel. One of ordinary skilled in the art would readily realize the suitable numbers with proper position and size to support open channels from collapsing when negative pressure applies to the flexible tube.

Referring to FIGS. 14A-F, another variation of the invention oral device comprising open channels connected with the posterior end without middle openings to deliver negative pressure from posterior part to anterior part of oral cavity is shown in various views. The oral device shown comprises a shield 1450 to be situated between lips and front teeth, a tube passing through the shield, and a negative pressure deliverable part (i.e., a flexible tube 1410, which is part of or in connection with the tube passing through the shield), several open channels 1441 (e.g., two shown in the figures) connecting with the posterior end 1430 with indentation, and a tongue protector 1460. In some embodiments, as illustrated in FIGS. 13 D and 13E, the flexible tube further comprises several supports within the flexible tube to support the open channel from collapsing during the application of negative pressure. In some embodiments, the flexible tube comprises 1 to 20, 1 to 15, 1 to 10, 1 to 7, 1 to 6, 1 to 5, 1 to 4, 1 to 2, or one support(s). The size and the position of the supports depend on the length of the open channel. One of ordinary skilled in the art would readily realize the suitable numbers with proper position and size to support open channels from collapsing when negative pressure applies to the flexible tube.

Besides the flexible tube to accommodate different contours of the upper palate of patients, the oral device has fold lines 1454 (which are bendable) and recesses 1453 to allow the device conformable to different anatomy of jaws, front teeth and lips of different patients. The fold lines 1454 on the shield allow the shield to be pliable and compliant to the tooth orientations and shapes. The recesses 1453 near the joint where the tube passing through allow the flexible tube 1410 to bend freely. The indentation at the posterior end prevents the posterior end opening to be totally blocked by soft tissues. In this embodiment, there are no middle openings but yet the negative pressure is delivered from posterior part to anterior part of oral cavity via the open channels.

Referring to FIGS. 15A to 15E, another variation of the invention oral device comprising an extended tongue protector combining the function of tongue protection and a flexible negative pressure deliverable part is shown in various views. The oral device shown comprises a shield 1550 (which is disposed between the front teeth and the lips), a tube 1542 passing through the shield, an extended tongue protector 1560, one or more middle opening 1540 (e.g., one shown) near the center of the shield 1550 where the middle opening is connected to several open channels 1541 (e.g., three open channels shown). FIGS. 15A, 15B and 15C are the top plan view, front view and back view of the oral device respectively. As illustrated in FIGS. 15A, a number of open channels 1541 are located on an upper surface of the flexible tube. Further, FIGS. 15B and 15C show more details of the oral device. Each open channel 1541 defines a groove having a length extending along the length of the tube 1510 and a depth extending inward from one of the upper side of the tube. The flexible extended tongue protector covers both anterior and top regions of the tongue, which is pre-shaped to adapt (conform) the shape of upper palate (providing better fit of tongue shapes), thus allow patients to easily wear the oral device. The open channels on the extended tongue protector are connected to the middle opening (without posterior end openings) to deliver negative pressure from anterior part to posterior part of oral cavity. Multiple open channels distribute negative pressure more evenly.

Referring to FIGS. 16A to 16E, another variation of the invention oral device comprising a pre-bended flexible tube with an integrated tongue protector is shown in various views. These figures illustrate another embodiment where a tongue protector is connected with the flexible tube, not with the shield as described before. The oral device shown comprises a shield 1650 (which is disposed between the front teeth and the lips), a negative pressure deliverable part (i.e., a pre-bended flexible tube 1660) passing through the shield, a tongue protector 1660, where the tongue protector is integrated on the pre-bended tube. The pre-bended tube is shaped to adapt (conform) the shape of upper palate allowing patients to easily wear the oral device. The integrated tongue protector on the pre-bended tube adapts (conform) to tongue shapes allowing proper tongue protection.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An oral device comprising:
a shield configured to be situated between lips and front teeth of a user, and
a tube passing through the shield, wherein the tube comprises a flexible negative pressure deliverable part configured to be inserted into an open space between a tongue and an upper palate of the user, the flexible negative pressure deliverable part defining a longitudinal passage configured to be in fluid communication with the open space when the flexible negative pressure deliverable part is inserted into the open space, wherein the oral device is configured to deliver negative pressure to the open space via the longitudinal passage of the flexible negative pressure deliverable part to draw the tongue in a superior direction to the upper palate to close the open space between the tongue and the upper palate of the user, wherein the flexible negative pressure deliverable part of the tube is configured to conform to the contour of the upper palate when the tongue is drawn in the superior direction to the upper palate to close the open space between the tongue and the upper palate;
wherein the flexible negative pressure deliverable part further comprises a middle opening in fluid communication with the longitudinal passage at one end of the middle opening and in fluid communication with the open space at another end of the middle opening to deliver negative pressure to the open space when the flexible negative pressure deliverable part is inserted into the open space, and an open channel in fluid communication with the transverse middle opening and extending longitudinally along an external side of the flexible negative pressure deliverable part, the open channel distributing the negative pressure into the open space and preventing the transverse middle opening from obstruction by the tongue.

2. The oral device of claim 1, wherein the open channel extends to a posterior end of the tube.

3. The oral device of claim 1, wherein the shield comprises a bendable structure configured to be conformable to the shape of front teeth and lips of the user.

4. The oral device of claim 1, wherein the shield further functions as a seal.

5. The oral device of claim 1, wherein the shield further comprises at least one air vent.

6. The oral device of claim 5, wherein the at least one air vent is configured to allow the lips of the user to cover the air vent.

7. The oral device of claim 5, wherein the at least one air vent comprises a one-way valve.

8. The oral device of claim 1, wherein the shield includes recesses at a location where the tube passes through the shield to allow the tube to bend freely relative to the shield.

9. The oral device of claim 1, wherein the negative pressure deliverable part defines a longitudinal axis extending between anterior and posterior ends of the negative pressure deliverable part, the longitudinal passage extending in a direction generally parallel to the longitudinal axis, and wherein the posterior end of the flexible negative pressure deliverable part defines an open posterior end of the longitudinal passage, the open posterior end of the longitudinal passage configured to be in fluid communication with the open space when the posterior end of the flexible negative pressure deliverable part is inserted into the open space.

10. The oral device of claim 1, wherein the open channel comprises an elongate opening in an exterior surface of the flexible negative pressure deliverable part.

11. The oral device of claim 1, wherein the tube comprises an anterior end connected to a vacuum source, the flexible negative pressure deliverable part of the tube being more flexible than the anterior end.

12. The oral device of claim 11, wherein the vacuum source is controlled by a negative control system.

13. The oral device of claim 1, wherein the shield has fold lines configured to enable the shield to be pliable and compliant to the orientations and shapes of the teeth and lips of the user.

14. The oral device of claim 1, wherein the tube is wider at a posterior end of the flexible negative pressure deliverable part to provide rigidity in the tube.

15. The oral device of claim 14, wherein the posterior end of the flexible negative pressure deliverable part has a curved edge.

16. The oral device of claim 1, wherein the oral device further comprises a tongue protector configured to prevent direct impingement of the teeth of the user on the tongue of the user.

17. The oral device of claim 16, wherein the tongue protector is configured to be disposed between a bottom of the tongue of the user and a back side of lower front teeth of the user.

18. The oral device of claim 17, wherein the tongue protector further comprises an indentation sized and shaped to accommodate a size and shape of a tongue frenulum of the tongue of the user.

19. The oral device of claim 1, wherein the tube and the shield are detachable.

20. The oral device of claim 19, where the detachable tube and detachable shield are selected from a group of possible detachable tubes and possible detachable shields that are interchangeable and have different sizes so that the detachable tube and detachable shield selected are of a size that fits the user's anatomy.

21. The oral device of claim 19, wherein the detachable tube is slidable.

22. The oral device of claim 1, wherein the flexible negative pressure deliverable part further comprises 1 to 20 supports extending from the flexible negative pressure deliverable part to support the open channel from collapsing during the application of negative pressure.

23. The oral devices of claim 1, wherein the flexible negative pressure deliverable part comprises an extended tongue protector and is connected to the shield.

24. The oral device of claim 23, wherein the extended tongue protector has at least one open channel.

25. The oral device of claim 24, wherein the extended tongue protector is integrated on the negative pressure deliverable part.

26. A system for closing the open space between the tongue and the upper palate of the user comprising the oral device of claim 1 and a negative pressure control system including a vacuum source.

27. A method for closing the open space between the tongue and the upper palate of the user comprising:
   positioning the flexible negative pressure deliverable part of the oral device of claim 1 in the open space between the tongue and the upper palate of the user; and
   applying a negative pressure via the oral device to the open space to draw the tongue in the superior direction to the upper palate to close the open space between the tongue and upper palate.

28. A method for closing the open space between the tongue and the upper palate of the user comprising:
   positioning the flexible negative pressure deliverable part of the oral device of claim 1 in the open space between the tongue and the upper palate of the user; and
   applying a negative pressure via the oral device to the open space to draw the tongue in the superior direction to the upper palate to close the open space between the tongue and upper palate, wherein at least a portion of the negative pressure being applied to the open space is applied via the open channel.

* * * * *